United States Patent [19]

Klemarczyk et al.

[11] Patent Number: 4,485,828
[45] Date of Patent: Dec. 4, 1984

[54] USE OF SUBSTITUTED METHYL ISOPROPYL CYCLOHEXENONES IN AUGMENTING OR ENHANCING THE AROMA OR TASTE OF SMOKING TOBACCO COMPOSITIONS AND SMOKING TOBACCO ARTICLE COMPONENTS

[75] Inventors: Philip T. Klemarczyk, Old Bridge; Lambert Dekker, Wyckoff, both of N.J.; Jacob Kiwala, Brooklyn, N.Y.

[73] Assignee: International Flavors & Fragrances Inc., New York, N.Y.

[21] Appl. No.: 492,013

[22] Filed: May 5, 1983

Related U.S. Application Data

[62] Division of Ser. No. 343,580, Jan. 28, 1982, Pat. No. 4,400,311.

[51] Int. Cl.$^3$ .................. A24B 3/12; A24B 15/30; A24D 1/00
[52] U.S. Cl. .................................................. 131/276
[58] Field of Search ........................... 131/276, 275

[56] References Cited

U.S. PATENT DOCUMENTS 4,352,943 10/1982 Kaiser et al. .................... 252/522 R

FOREIGN PATENT DOCUMENTS 0049831 3/1969 Fed. Rep. of Germany ... 252/522 R

OTHER PUBLICATIONS

Wiemann et al., Ann. Chim., 1972, vol. 7, pp. 399–499.
Riand et al, Bulletin de la Societe Chim. de France, 1976, Nos. 3-4, pp. 557–562.
Arcantder, *Perfume and Flavor Chemicals*, vol. II, Monographs, 1932, 2457, 2930.

*Primary Examiner*—V. Millin
*Attorney, Agent, or Firm*—Arthur L. Liberman

[57] ABSTRACT

Described is a process for augmenting or enhancing the aroma or taste of smoking tobacco compositions and/or smoking tobacco article components comprising the step of adding to a smoking tobacco composition and/or smoking tobacco article component, an aroma or taste augmenting or enhancing quantity of at least one compound defined according to the structure:

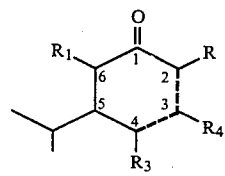

wherein one of the dashed lines represents a carbon-carbon double bond and the other of the dashed lines represents a carbon-carbon single bond; wherein $R_4$ represents methyl or ethyl; wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:

(i) when the dashed line at the 3-4 position is a double bond, then $R_3$ is hydrogen or 2-methyl-1-propenyl;
(ii) when the dashed line at the 2-3 position is a double bond, then $R_2$ is hydrogen or 2-methyl-1-propenyl;
(iii) when $R_4$ is ethyl, then $R_2$ is methyl and the double bond is at the 2-3 position; and
(iv) when $R_4$ is methyl, then $R_2$ is hydrogen; 2-methyl-1-propenyl or 2-methyl-1-propylidenyl;

with the members of said genus being novel compounds when $R_4$ is ethyl or when $R_4$ is methyl and the double bond is at the 3-4 position or when $R_4$ is methyl and the double bond is at the 2-3 position with $R_3$ being hydrogen.

3 Claims, 44 Drawing Figures

GLC PROFILE FOR EXAMPLE A

GLC PROFILE FOR EXAMPLE A.

GLC PROFILE FOR EXAMPLE I.
CRUDE REACTION PRODUCT.

IR SPECTRUM FOR EXAMPLE A.

GLC PROFILE FOR EXAMPLE I. (BULKED DISTILLATION FRACTIONS 11-19).

NMR SPECTRUM FOR PEAK 1 OF EXAMPLE I.

IR SPECTRUM FOR PEAK 2 OF EXAMPLE I.

NMR SPECTRUM FOR PEAK 2 OF EXAMPLE I.

IR SPECTRUM FOR EXAMPLE I, PEAK 2.

NMR SPECTRUM FOR PEAK 3 OF EXAMPLE I.

IR SPECTRUM FOR PEAK 3 OF EXAMPLE I.

NMR SPECTRUM FOR PEAK 4A OF EXAMPLE I.

IR SPECTRUM FOR PEAK 4A OF EXAMPLE I.

NMR SPECTRUM FOR PEAK 4B OF EXAMPLE I.

IR SPECTRUM FOR PEAK 4B OF EXAMPLE I.

NMR SPECTRUM FOR PEAK 5 FOR EXAMPLE I.

IR SPECTRUM FOR EXAMPLE I PEAK 5.

GLC PROFILE FOR EXAMPLE III.

GLC PROFILE FOR EXAMPLE I, (BULKED FRACTIONS 11-19).

GLC PROFILE FOR EXAMPLE II.
REACTION PRODUCT

GLC PROFILE FOR EXAMPLE II
BULKED FRACTIONS 7-17.

NMR SPECTRUM FOR PEAK I OF EXAMPLE III.

IR SPECTRUM FOR PEAK I OF EXAMPLE III.

NMR SPECTRUM FOR PEAK 2 FOR EXAMPLE III.

IR SPECTRUM FOR PEAK 2 OF EXAMPLE III.

NMR SPECTRUM FOR PEAK 3 OF EXAMPLE III.

IR SPECTRUM FOR PEAK 3 OF EXAMPLE III.

GLC PROFILE FOR EXAMPLE IV(B)

GLC PROFILE FOR EXAMPLE IV(C)

GLC PROFILE FOR EXAMPLE IV(D)

GLC PROFILE FOR EXAMPLE IV(E)

GLC PROFILE FOR EXAMPLE IV(F)

GLC PROFILE FOR EXAMPLE IV(G)

GLC PROFILE FOR EXAMPLE IV(H).

GLC PROFILE FOR EXAMPLE IV(J).

GLC PROFILE FOR EXAMPLE IV(K).

GLC PROFILE FOR EXAMPLE IV(L).

GLC PROFILE FOR EXAMPLE IV(M)

GLC PROFILE FOR EXAMPLE V.

GLC PROFILE FOR EXAMPLE V BULKED FRACTIONS 8-15.

GLC PROFILE FOR EXAMPLE VI.
(2 HOUR SAMPLE)

GLC PROFILE FOR EXAMPLE VI.
BULKED FRACTIONS 7-20

GLC PROFILE FOR EXAMPLE VII.
REACTION PRODUCT.

GLC PROFILE FOR EXAMPLE VII.
BULKED FRACTIONS 6-16.

USE OF SUBSTITUTED METHYL ISOPROPYL CYCLOHEXENONES IN AUGMENTING OR ENHANCING THE AROMA OR TASTE OF SMOKING TOBACCO COMPOSITIONS AND SMOKING TOBACCO ARTICLE COMPONENTS

This is a divisional of application Ser. No. 343,580 filed 1/28/82 now U.S. Pat. No. 4,400,311 issued on Aug. 23, 1983.

BACKGROUND OF THE INVENTION

The instant invention provides substituted 3-alkyl-5-isopropyl cyclohexenones a number of which are novel, defined according to the structure:

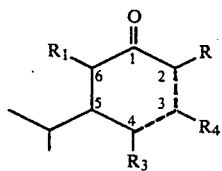

wherein one of the dashed lines represents a carbon-carbon double bond and the other of the dashed lines represents a carbon-carbon single bond; wherein $R_4$ represents methyl or ethyl; wherein one of $R_1$, $R_2$ or $R_3$ represents 2-methyl-1-propenyl or 2-methyl-1-propylidenyl and other of $R_1$, $R_2$ and $R_3$ represents hydrogen; with the provisos that:

(i) when the dashed line at the 3-4 position is a double bond, $R_3$ is hydrogen or 2-methyl-1-propenyl;
(ii) when the dashed line at the 2-3 position is a double bond, $R_2$ is hydrogen, methyl or 2-methyl-1-propenyl;
(iii) when $R_4$ is ethyl, then $R_2$ is methyl and the double bond is at the 2-3 position; and
(iv) when $R_4$ is methyl, when $R_2$ is hydrogen; 2-methyl-1-propenyl or 2-methyl-1-propylidenyl;

with the members of said genus being novel compounds when $R_4$ is ethyl or when $R_4$ is methyl and the double bond is at the 3-4 position or when $R_4$ is methyl and the double bond is at the 2-3 position with $R_3$ being hydrogen.

Chemical compounds which can provide peppery, sweaty, guiacwood-like, green, burnt grass, vetiver-like, sandalwood-like, fresh, floral, citrusy and spicy aroma nuances with sauge sclaree topnotes and musky undertones are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide woody, peppery and citrusy aroma and taste nuances in smoking tobacco compositions and smoking tobacco article components prior to smoking and can impart a sweet, citrusy character to smoke flavor in smoking tobacco compositions and smoking tobacco articles on smoking are highly desirable in the art of smoking tobacco flavoring. Many of the natural materials which provide such aroma and taste nuances are high in cost, unobtainable at times, vary in quality from one batch to another and/or are generally subject to the usual variations of natural products.

There is, accordingly, a continuing effort to find synthetic materials which will replace, enhance, or augment the essential flavor and fragrance notes provided by natural essential oils or compositions thereof.

The fundamental problem in creating artificial flavor and fragrance agents is that the artificial flavor or fragrance to be achieved be as natural as possible. This generally proves to be a difficult task since the mechanism for flavor and/or fragrance development in many fragrance materials and tobacco products is not completely known. This is noticeable in products in the fragrance area having peppery, sweaty, guiacwood-like, green, burnt grass, vetiver-like, sandalwood-like, fresh, floral, citrusy and spicy aroma nuances with sauge sclaree topnotes and musky undertones and in the tobacco area for materials which provide woody, peppery and citrusy aroma and taste nuances to smoking tobacco prior to smoking and imparts a sweet, citrusy character to smoke flavor on smoking in the smoking tobacco compositions and in the smoking tobacco article components.

Arctander "Perfume and Flavor Chemicals (Aroma Chemicals)" Volume II, published by the author 1969 discloses at Monograph 1932, ten-carbon atom containing alkylidene methyl cycloalkenones, specifically, 3-methyl-5-n-butylidene cyclopenten-2-one defined according to the structure:

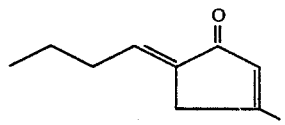

Arctander describes this compound as having a warm, caramellic, fruity odor reminiscent of strawberry; a sweet, fruity "cooked" strawberry flavor in dilutions below 20 ppm; and indicates that the ketone has been used and is "still used" to some extent in flavor compositions, rarely in perfumes. Arctander further states that this compound could be used as a modifier in fruity, floral bases since it blends excellently with the jasmone derivatives and isomers and also with the ionones.

Although substituted alkyl isopropyl cyclohexenones are known in the prior art, the disclosure of these substituted alkyl isopropyl cyclohexenones does not include the utilization thereof in perfumery and, furthermore, does not include processes for producing the substituted alkyl isopropyl cyclohexenones of our invention. Thus, Wiemann, et al and Riand and Brun in the references:

(i) Wiemann, et al, Ann. Chim., 1972, Volume 7, pages 399–499, title: "Contributions a L'Étude des Méchanismes de Condensations Catalytiques de Cétones β-Alkyl α-Éthyléniques en Milieu Hétérogène et en Phase Vapeur. Études Spectrographiques IR, UV, RMN".

(ii) Riand and Brun, Bulletin de la Societe Chimique de France, 1976, Nos. 3-4 (combined) pages 557–562 inclusive, title: "No. 105—Spectrométrie de Masse. II—Fragmentations Induites par Impact Électronique de Cyclohèxenones".

disclose the compounds having the structures:

produced by dimerization of the compound having the structure:

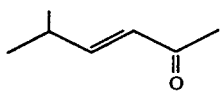

over magnesium oxide dimerization catalyst in the gas phase according to the reaction:

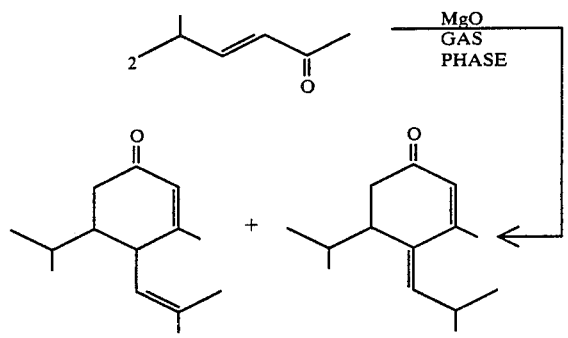

The prior art process of Riand and Brun or Wiemann, et al does not utilize a liquid phase dimerization and does not utilize the catalyst systems of our invention. Thus, the reaction mixture produced by Riand and Brun or Wiemann does not give rise to the same mixture of compounds as our invention and, furthermore, carrying out the process of our invention, we produce certain novel compounds not heretofore produced.

Unsaturated cyclic ketones with unsaturated alkylene and alkylidene side chains are known in the field of perfumery but these compounds are different in kind in structure from the structures of the compounds of the present invention. Thus, piperitenone having the structure:

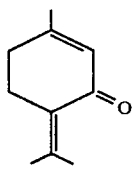

is disclosed by Arctander, "Perfume and Flavor Chemicals (Aroma Chemicals)" at Monograph No. 2628 to have a powerful, sharp, minty, bitter-herbaceous odor of moderate intensity. Arctander further states at Monograph No. 2629 that isopiperitenone having the structure:

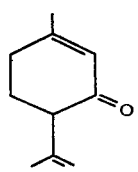

has a powerful, diffusive odor sweeter than that of piperitenone but equally minty, penetrating and of moderate tenacity. At Monograph No. 579, Arctander describes d-carvone having the structure:.

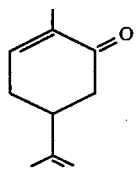

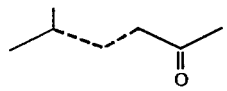

is produced wherein in the mixture in each of the molecules one of the dashed lines is a carbon-carbon double bond and the other of the dashed lines is a carbon-carbon single bond and the molecules are different.

Figure 2:
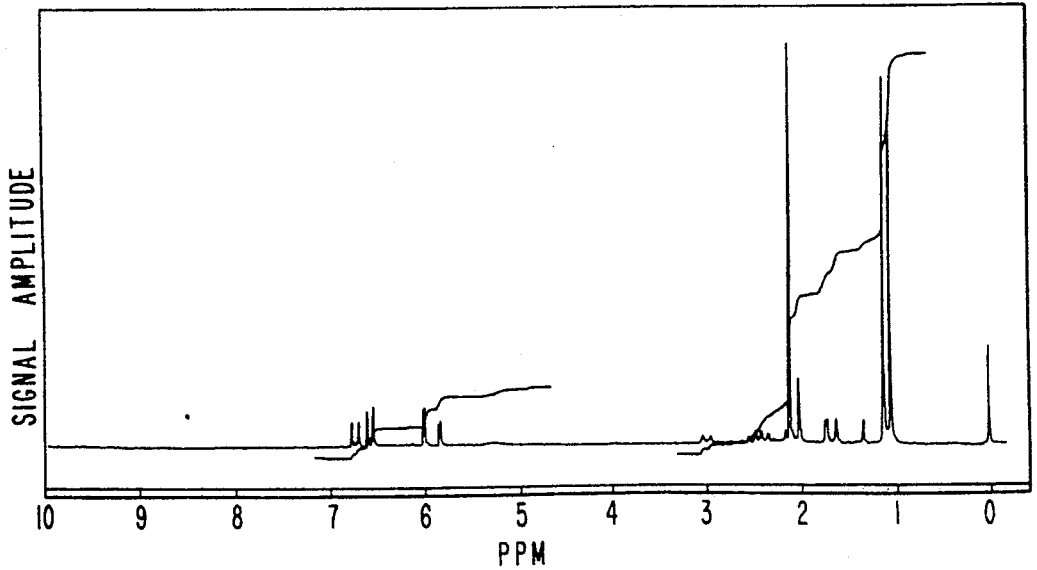

FIG. 2 is the NMR spectrum for the reaction product of Example A containing a mixture of compounds defined according to the structure:

wherein in the mixture in each of the molecules one of the dashed lines is a carbon-carbon double bond and the other of the dashed lines is a carbon-carbon single bond and the components of the mixture are different.

Figure 3:
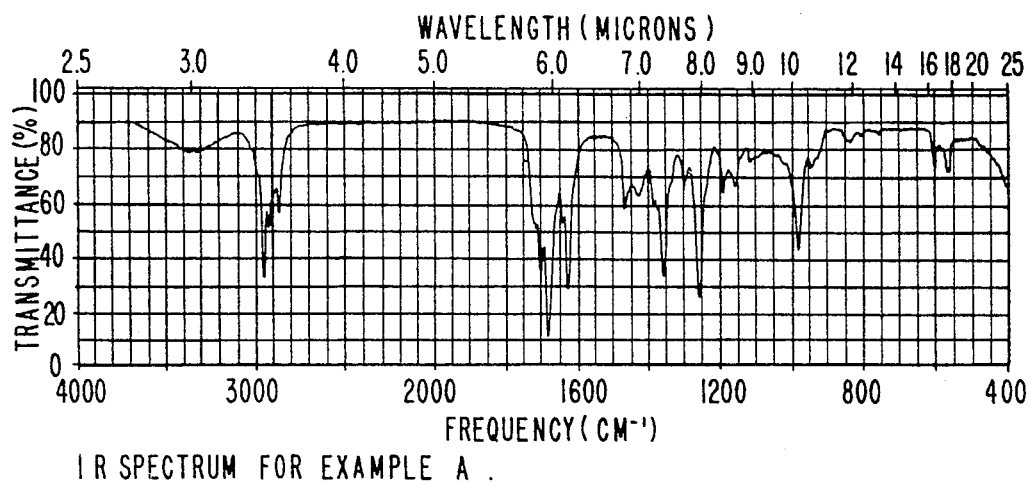

FIG. 3 is the infra-red spectrum for the reaction product of Example A containing the compounds defined according to the structure:

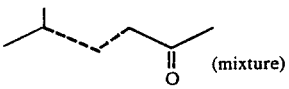

wherein in the mixture in each of molecules, one of the dashed lines is a carbon-carbon double bond and the other of the dashed lines is a carbon-carbon single bond and the compounds are different.

Figure 4:
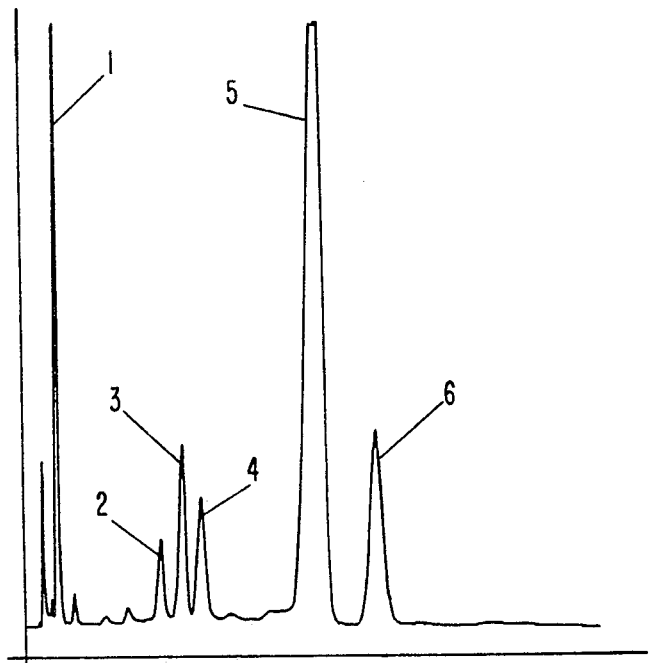

FIG. 4 is the GLC profile for the crude reaction product produced according to Example I containing a mixture of compounds defined according to the structures:

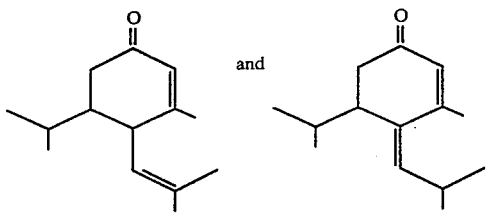

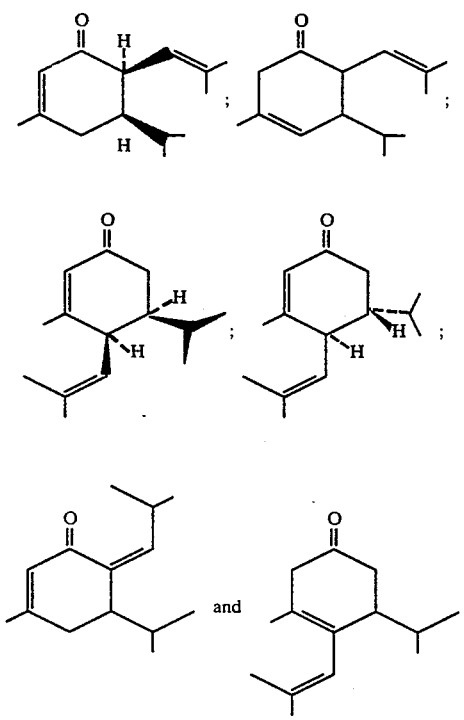

as well as the mixture of compounds which is the starting material for producing said compounds defined according to the structure:

Figure 5:
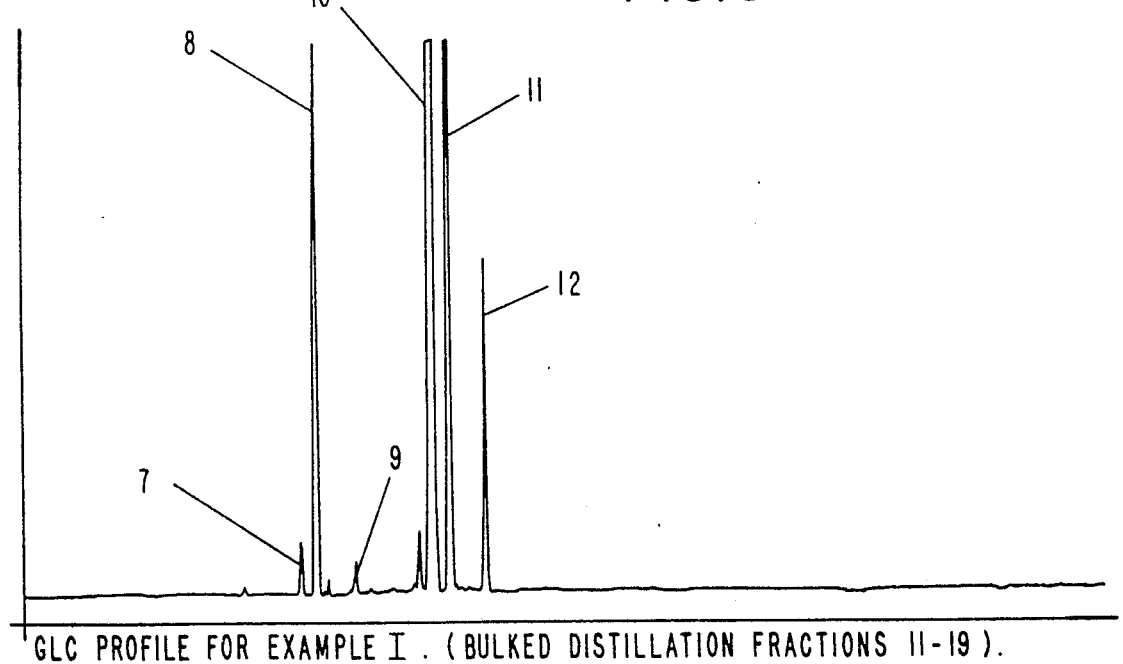

FIG. 5 is the GLC profile for the bulked distillation fractions 11-19 of the distillation product of the reaction product of Example I containing the compounds having the structures:

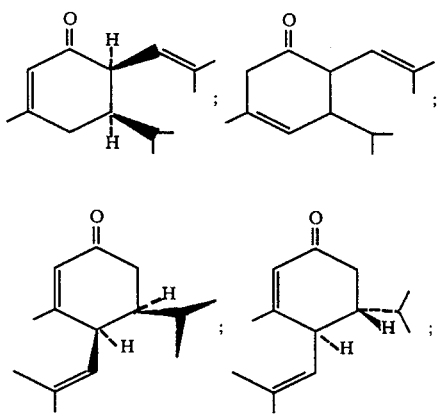

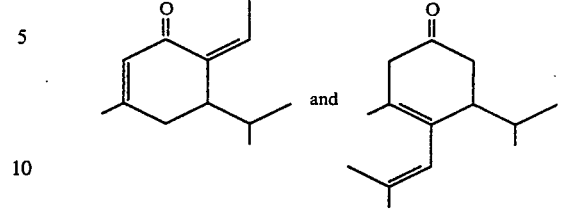

Figure 6:
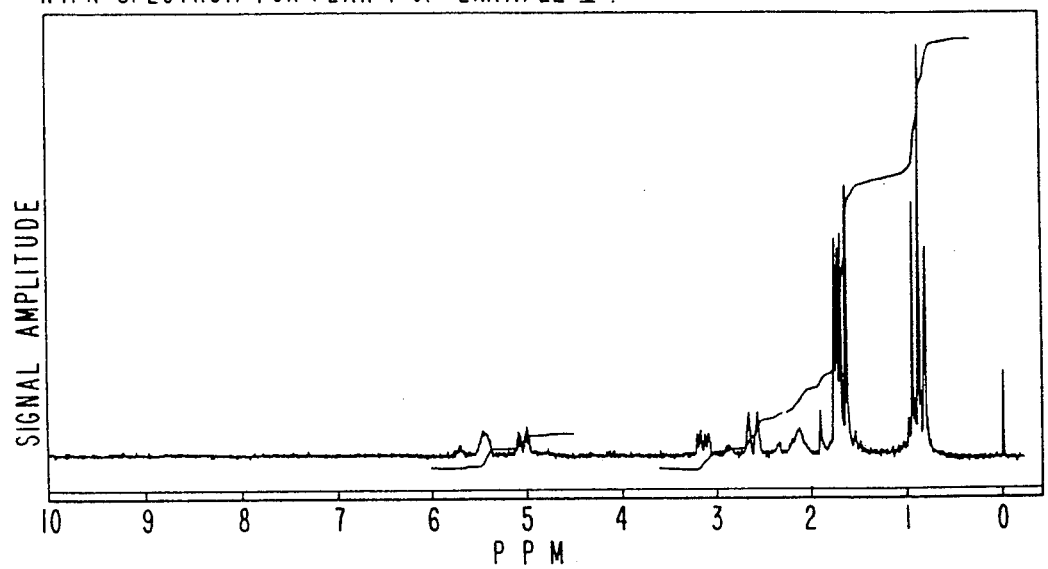

FIG. 6 is the NMR spectrum for Peak 1 (indicated by the reference numeral "2" on the GLC profile of FIG. 4, supra). The compound of Peak 1 has the structure:

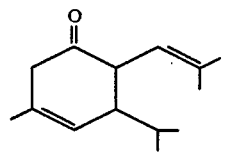

Figure 7:
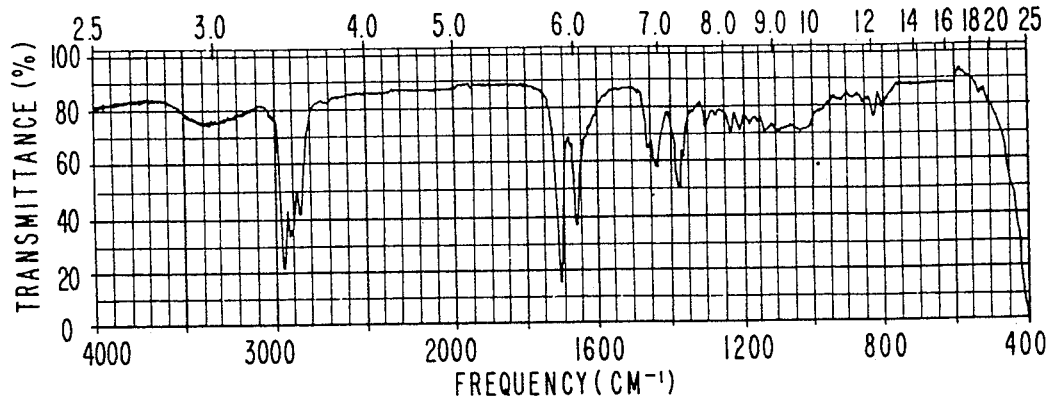

FIG. 7 is the infra-red spectrum for the compound of Peak 1 of the GLC profile of FIG. 4 having the structure:

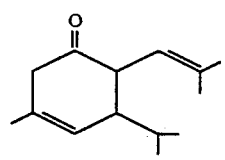

Figure 8:
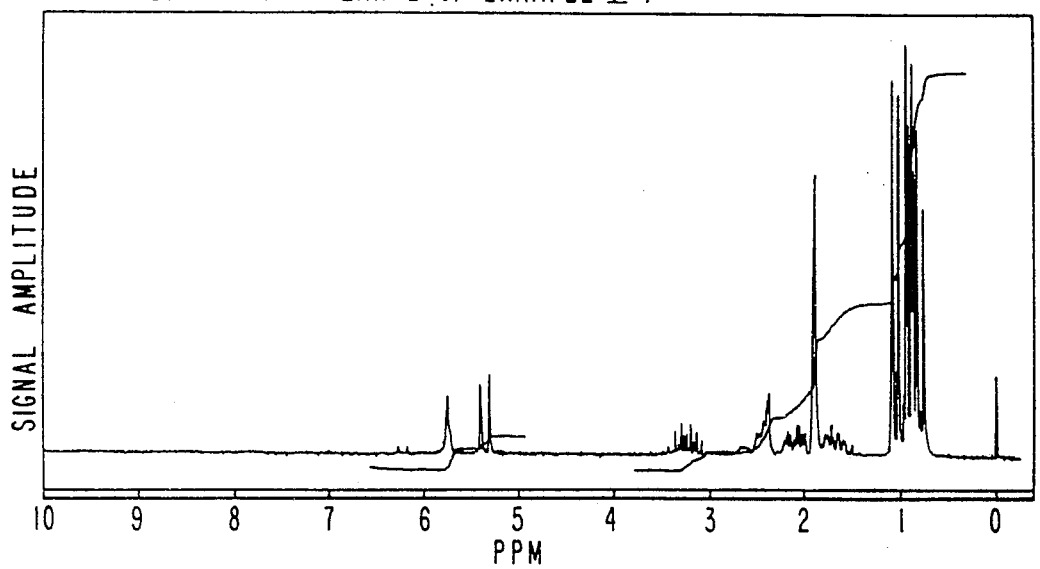

FIG. 8 is the NMR spectrum for Peak 2 of the GLC profile of FIG. 4 which is indicated by reference numeral "3" on said FIG. 4. Peak 2 signifies the compound having the structure:

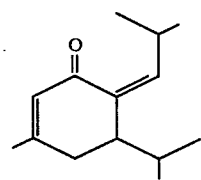

Figure 9:
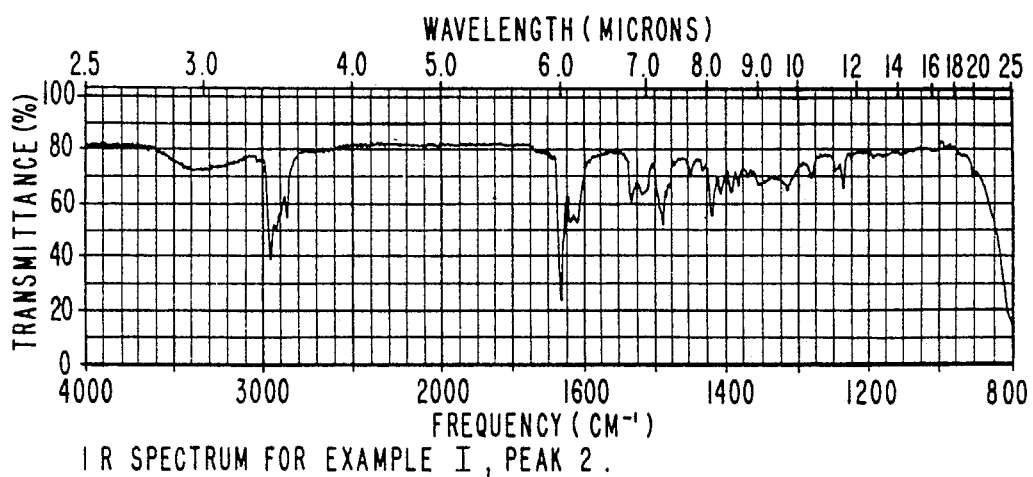

FIG. 9 is the infra-red spectrum for Peak 2 of the GLC profile of FIG. 4, containing the compound having the structure:

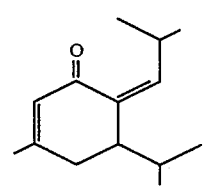

Figure 10:
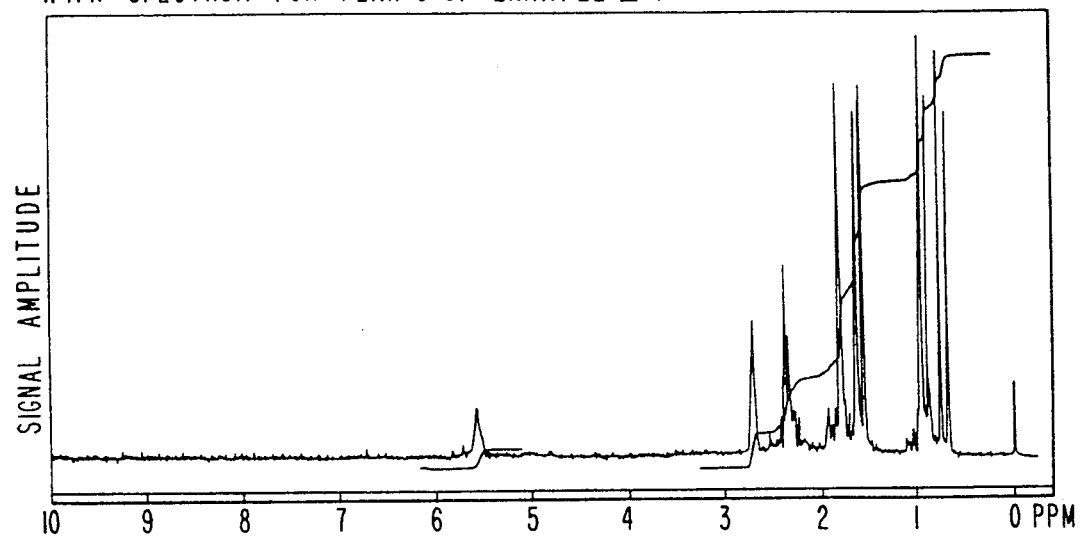

FIG. 10 is the NMR spectrum for Peak 3 of the GLC profile of FIG. 4, with Peak 3 being signified by the reference numeral "4". Peak 3 contains the compound having the structure:

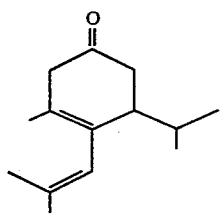

Figure 11:
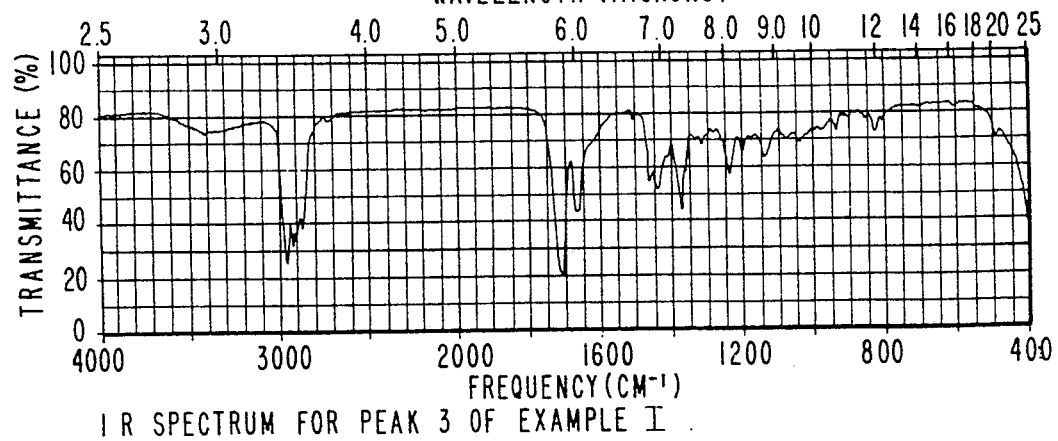

FIG. 11 is the infra-red spectrum for Peak 3 of the GLC profile of FIG. 4 which signifies the compound having the structure:

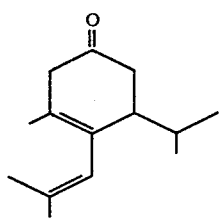

Figure 12:
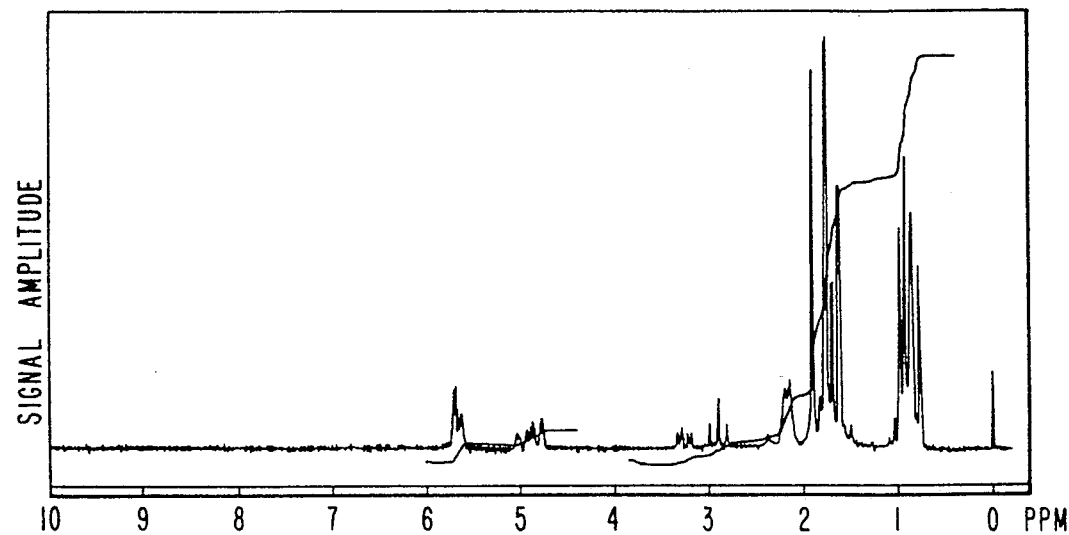

FIG. 12 is the NMR spectrum for Peak 4A of the GLC profile of FIG. 4 which signifies the compound having the structure:

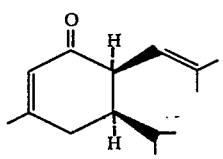

Peak 4A is indicated on FIG. 4 by reference numeral "5".

Figure 13:
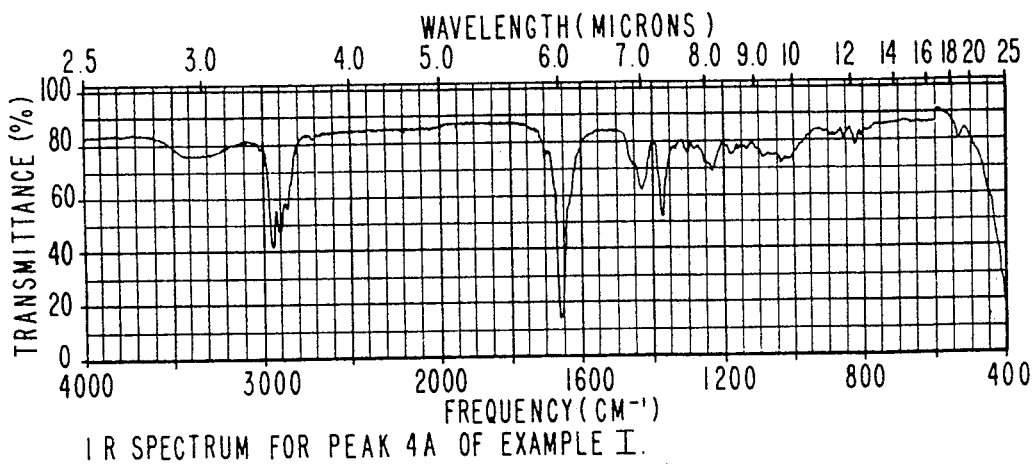

FIG. 13 is the infra-red spectrum for Peak 4A of the GLC profile of FIG. 4 signifying the compound having the structure:

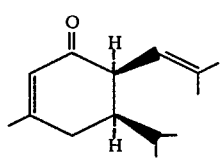

Figure 14:
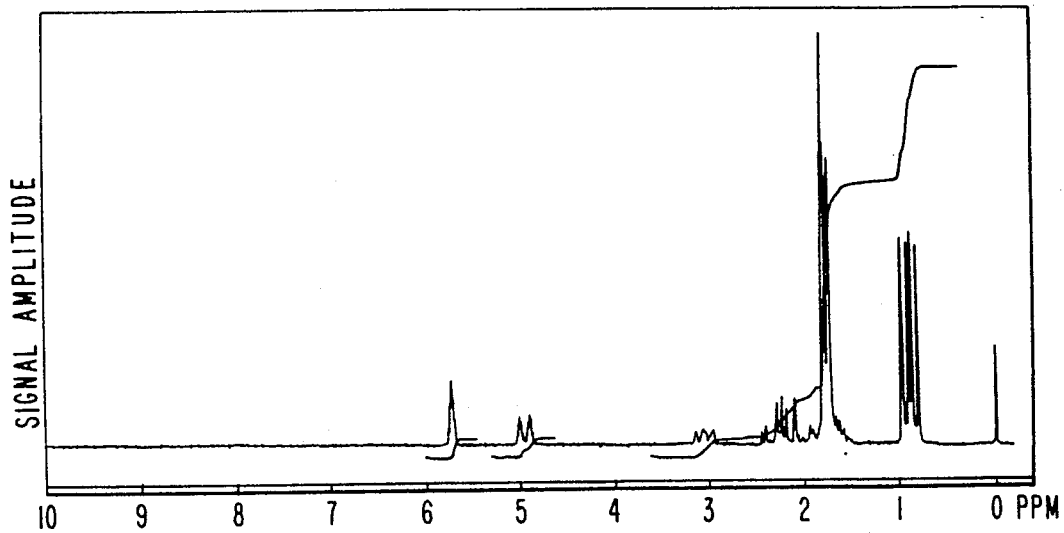

FIG. 14 is the NMR spectrum for Peak 4B of the GLC profile of FIG. 4 signifying the compound having the structure:

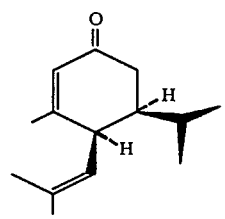

or the compound having the structure:

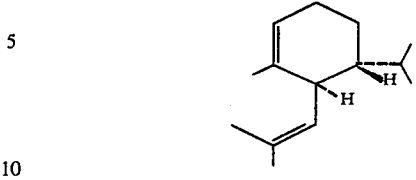

Peak 4B is indicated on FIG. 4 to have the reference numeral "5".

Figure 15:
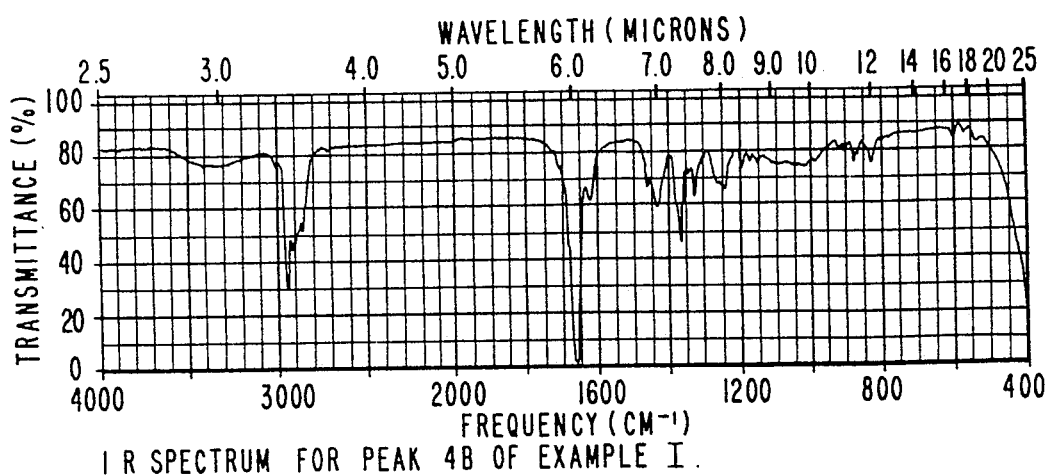

FIG. 15 is the infra-red spectrum for Peak 4B of the GLC profile of FIG. 4 which signifies one of the compounds having the structures:

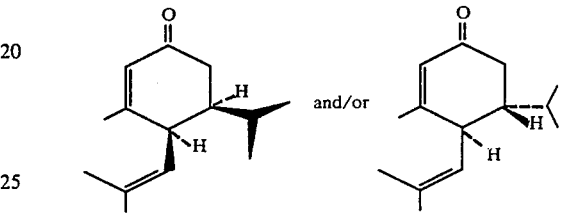

Peak 4B is shown by reference numeral "5" on FIG. 4.

Figure 16:
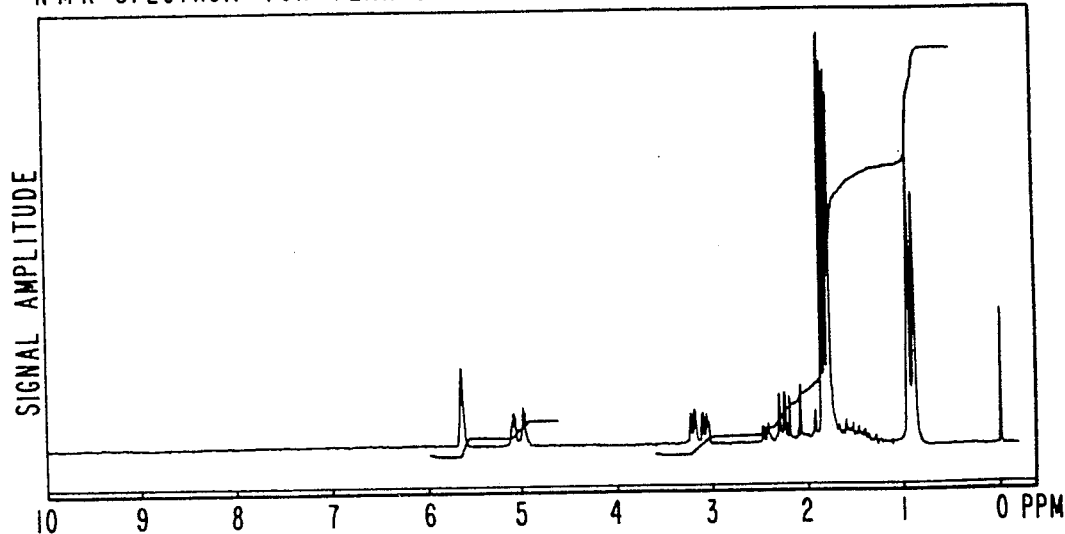

FIG. 16 is the NMR spectrum for Peak 5 of the GLC profile of FIG. 4 signifying the compounds having the structures:

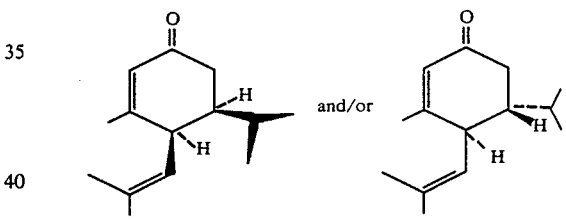

Peak 5 is indicated by the reference numeral "6" on FIG. 4.

Figure 17:
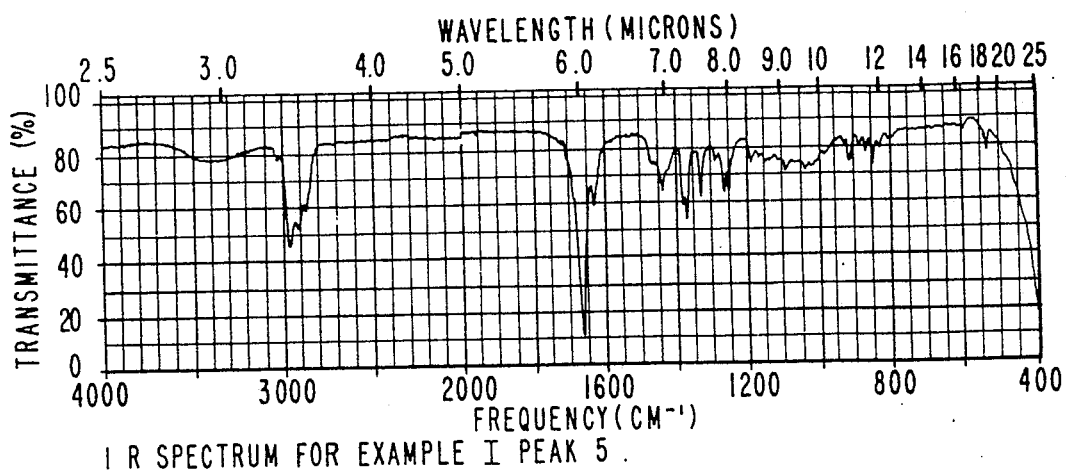

FIG. 17 is the infra-red spectrum for Peak 5 of the GLC profile of FIG. 4 signifying the compounds having the structures:

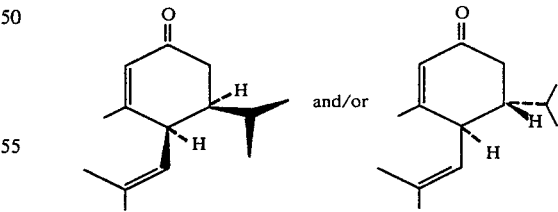

Peak 5 is indicated on FIG. 4 by reference numeral "6".

Figure 18:
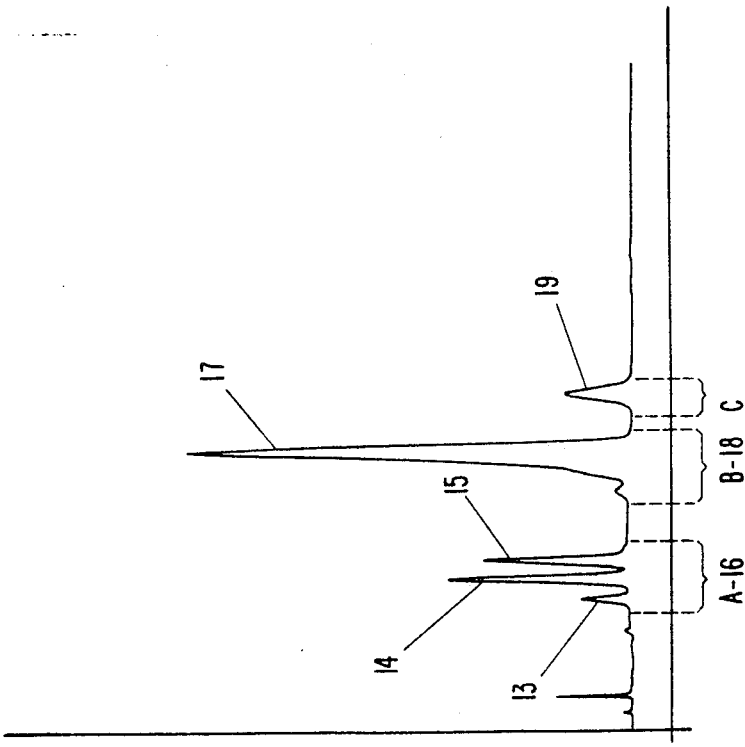

FIG. 18 is the GLC profile for bulked fractions 11–19 of Example I indicating groups of trapped peaks for organoleptic evaluations thusly:
  (i) Group "A" is the combination of Peaks 1, 2 and 3;
  (ii) Group "B" is Peak 4;
  (iii) Group "C" is Peak 5.

Figure 19A:
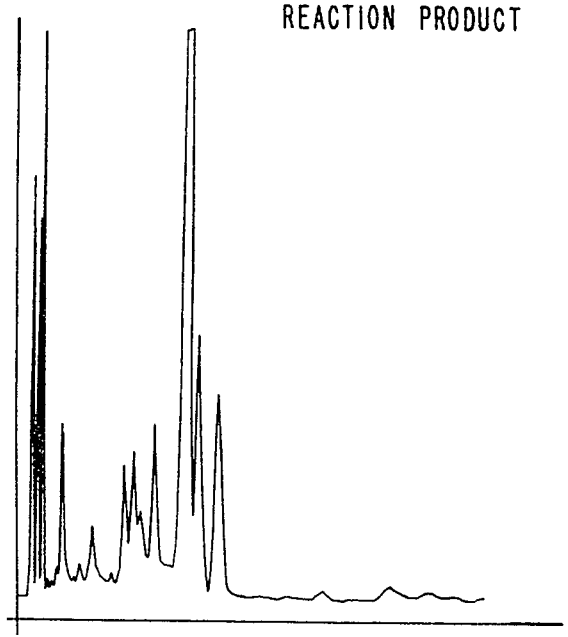

FIG. 19A is the GLC profile for the reaction product of Example II.

Figure 19B:
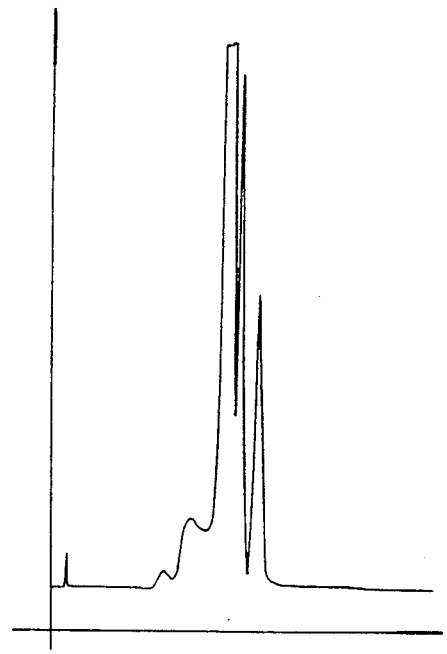

FIG. 19B is the GLC profile for the distillation product, bulked fractions 7-17 of the reaction product of Example II.

Figure 20:
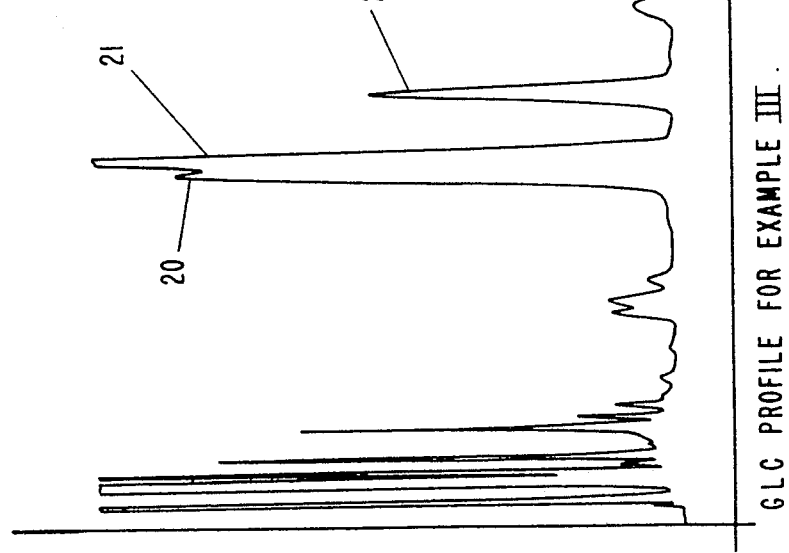

FIG. 20 is the GLC profile for the reaction product of Example III containing the compounds having the structures:

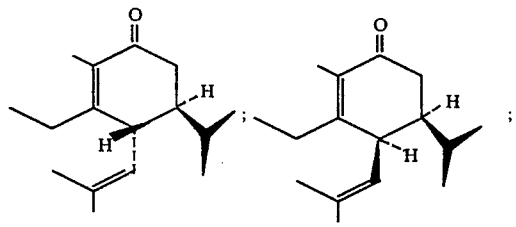

Figure 21:
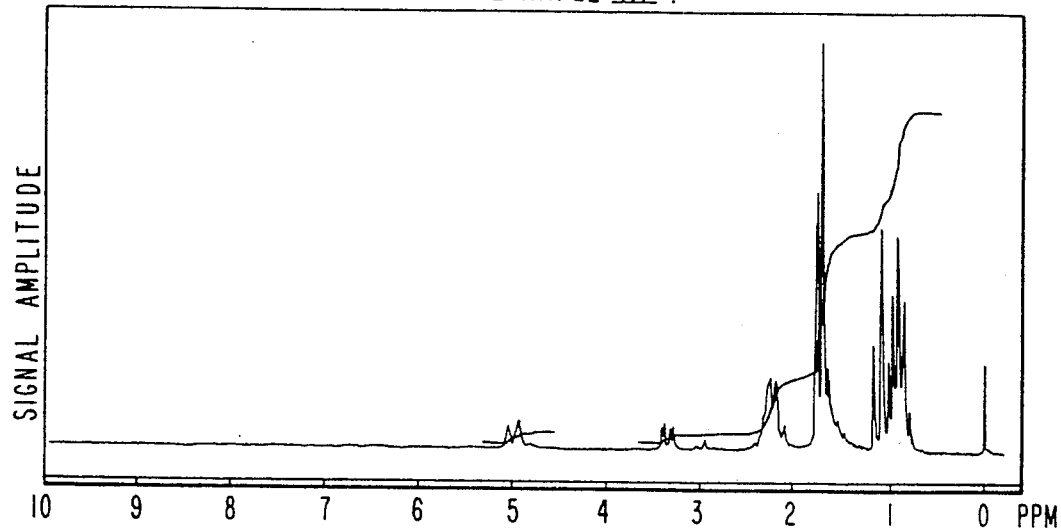

FIG. 21 is the NMR spectrum for Peak 1 of the GLC profile of FIG. 20 containing the compounds having the structures:

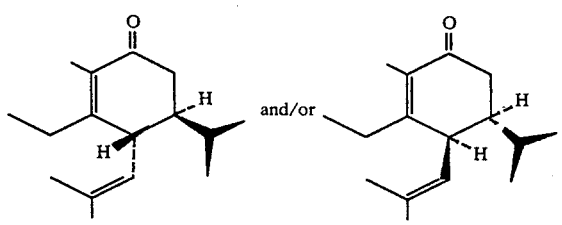

Figure 22:
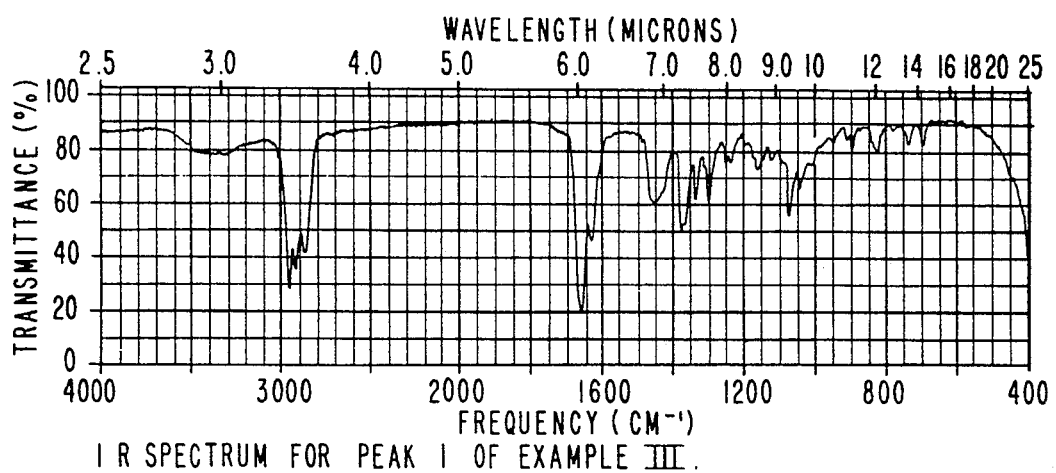

FIG. 22 is the infra-red spectrum for Peak 1 of the GLC profile of FIG. 20 containing the compounds having the structures:

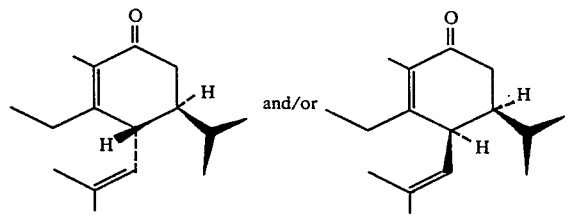

Peak 1 is signified by reference numeral "20" on FIG. 20.

Figure 23:
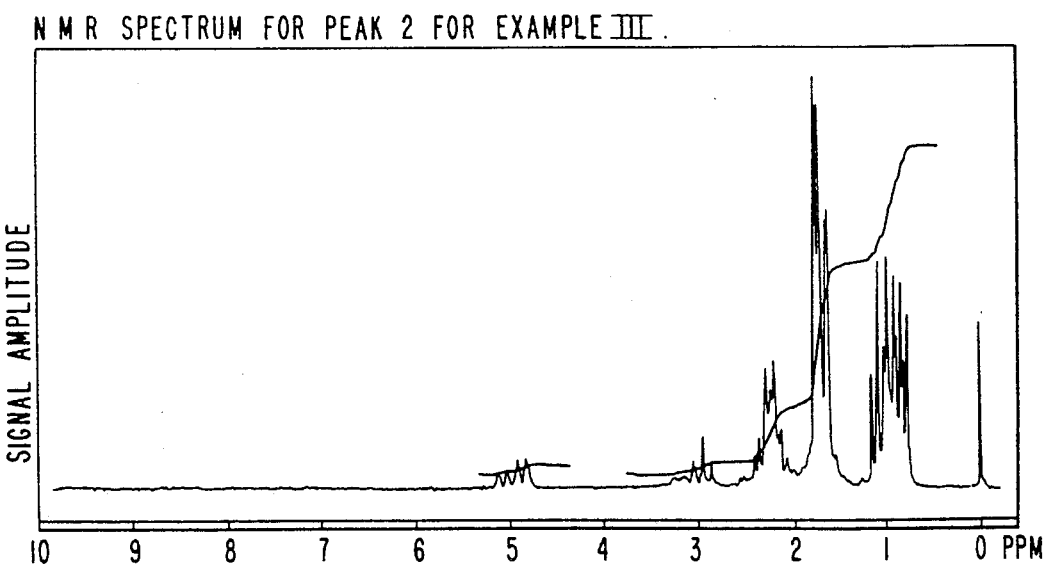

FIG. 23 is the NMR spectrum for Peak 2 of the GLC profile of FIG. 20 containing the compounds having the structures:

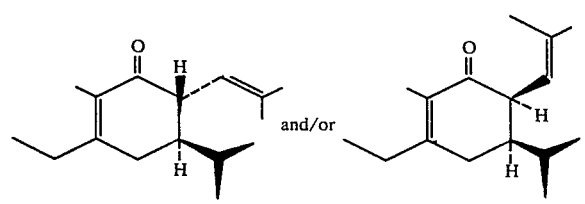

Peak 2 is indicated by reference numeral "21" on FIG. 20.

Figure 24:
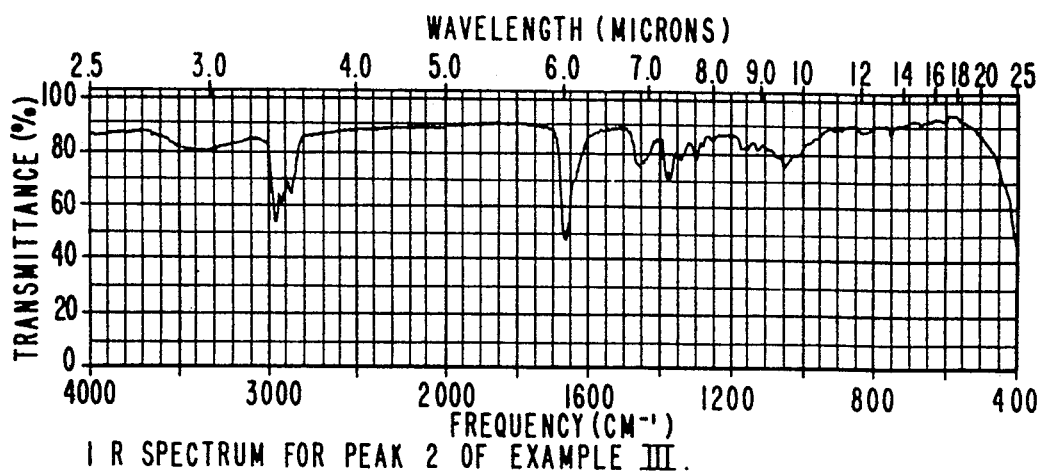

FIG. 24 is the infra-red spectrum for Peak 2 of the GLC profile of FIG. 20 containing the compounds having the structures:

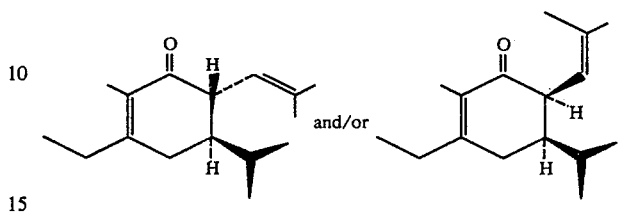

Figure 25:
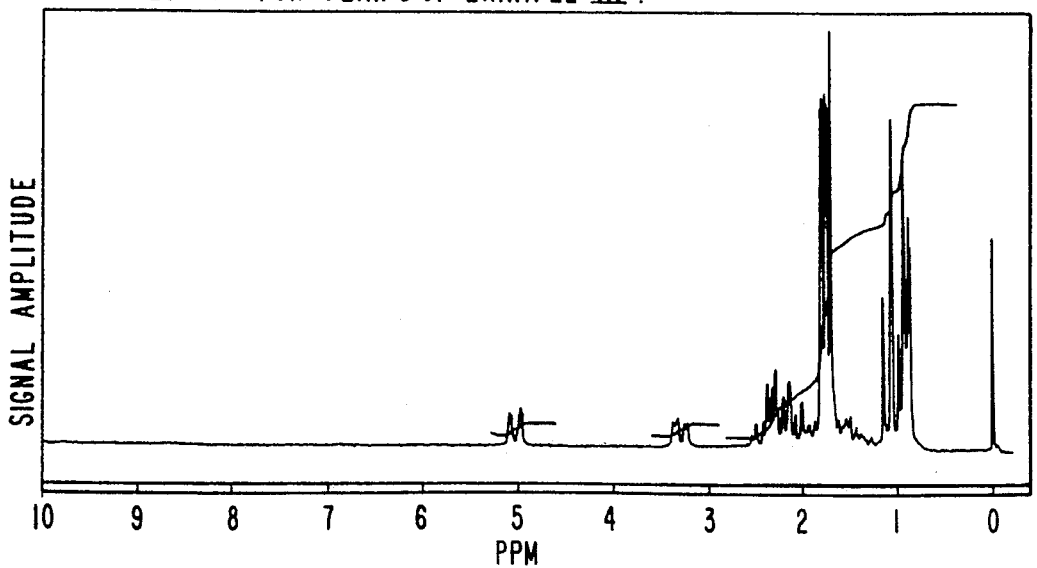

FIG. 25 is the NMR spectrum for Peak 3 of the GLC profile of FIG. 20 for the reaction product of Example III. Peak 3 contains the compounds having the structures:

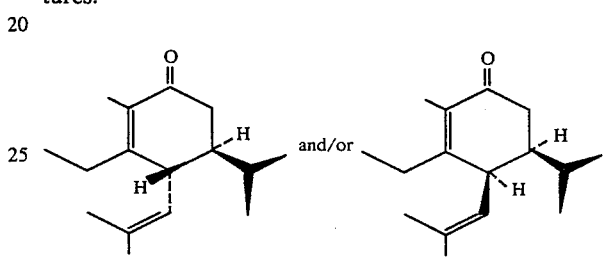

Peak 3 is indicated by reference numeral "22" on FIG. 20.

Figure 26:
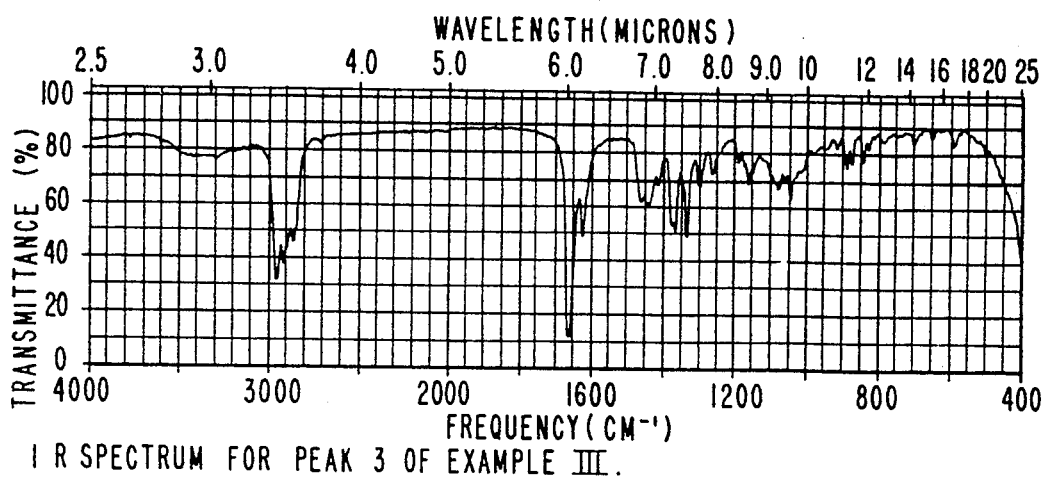

FIG. 26 is the infra-red spectrum for Peak 3 of the GLC profile of FIG. 20 containing the compounds having the structures:

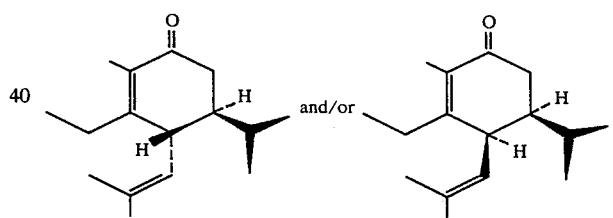

Figure 27:
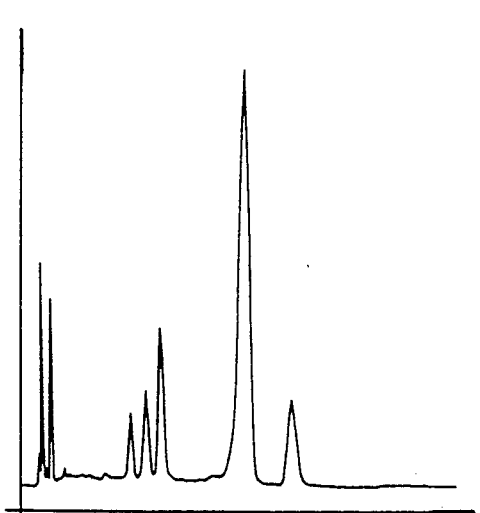

FIG. 27 is the GLC profile for the reaction product of Example IV(B).

Figure 28:
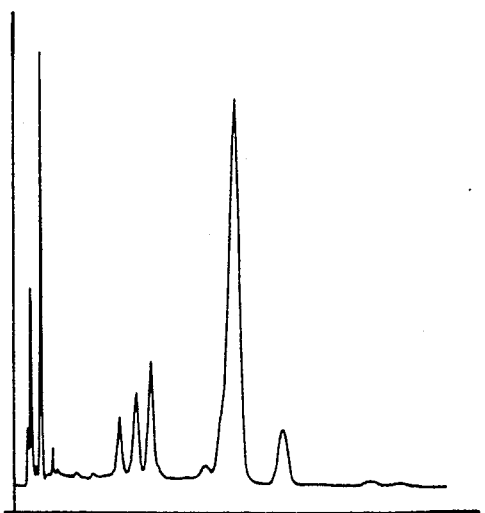

FIG. 28 is the GLC profile for the reaction product of Example IV(C).

Figure 29:
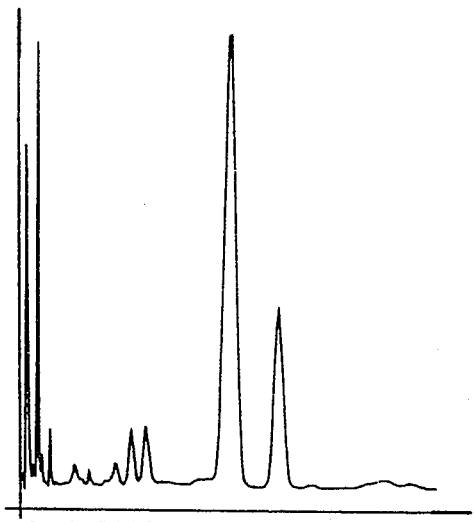

FIG. 29 is the GLC profile for the reaction product of Example IV(D).

Figure 30:
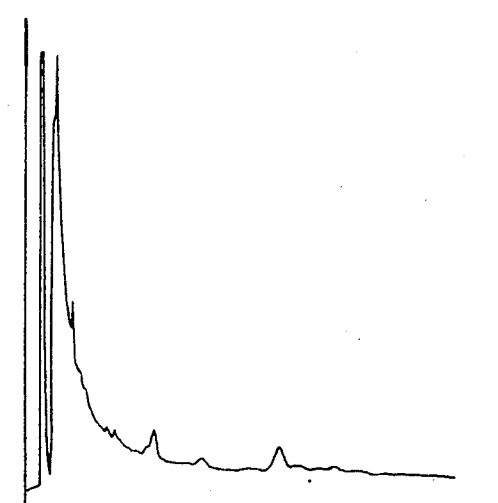

FIG. 30 is the GLC profile for the reaction product of Example IV(E).

Figure 31:
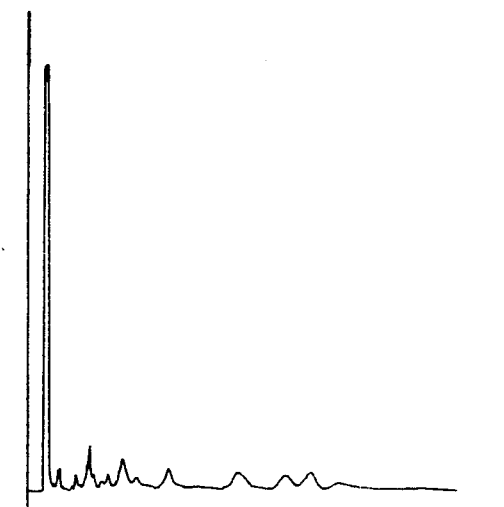

FIG. 31 is the GLC profile for the reaction product of Example IV(F).

Figure 32:
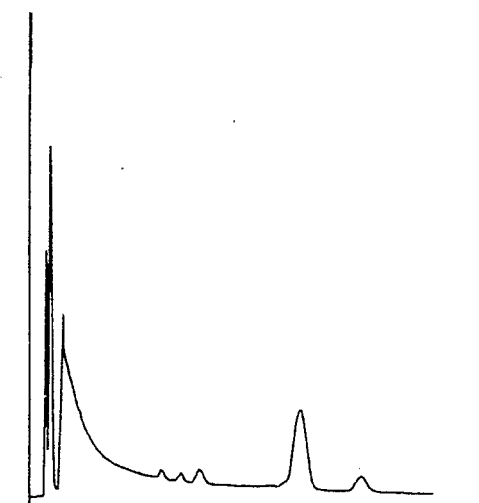

FIG. 32 is the GLC profile for the reaction product of Example IV(G).

Figure 33:
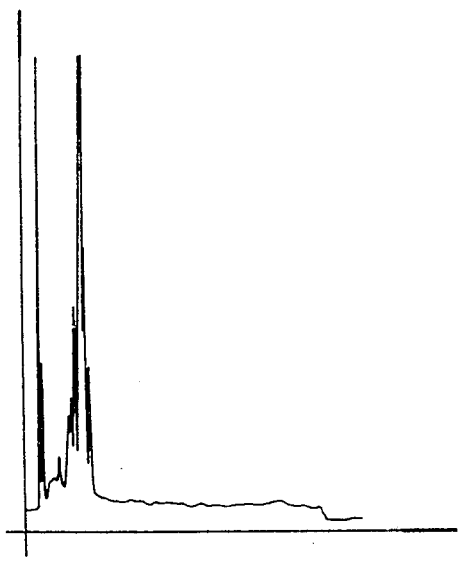

FIG. 33 is the GLC profile for the reaction product of Example IV(H).

Figure 34:
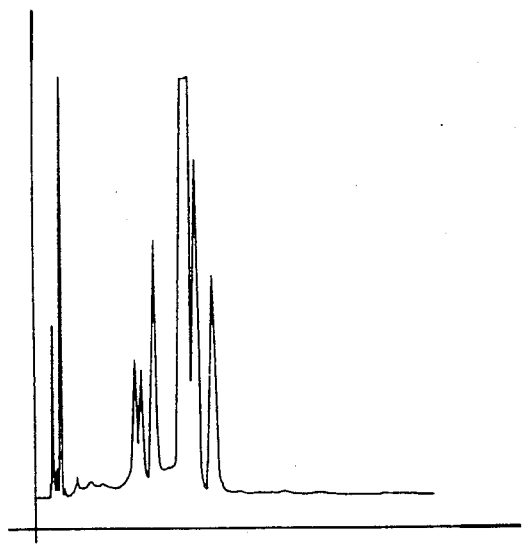

FIG. 34 is the GLC profile for the reaction product of Example IV(J).

Figure 35:
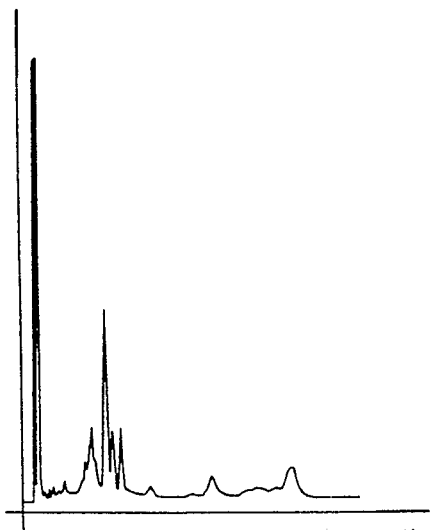

FIG. 35 is the GLC profile for the reaction product of Example IV(K).

Figure 36:
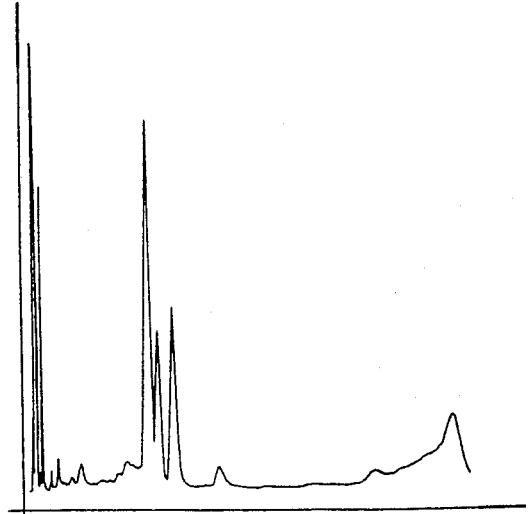

FIG. 36 is the GLC profile for the reaction product of Example IV(L).

Figure 37:
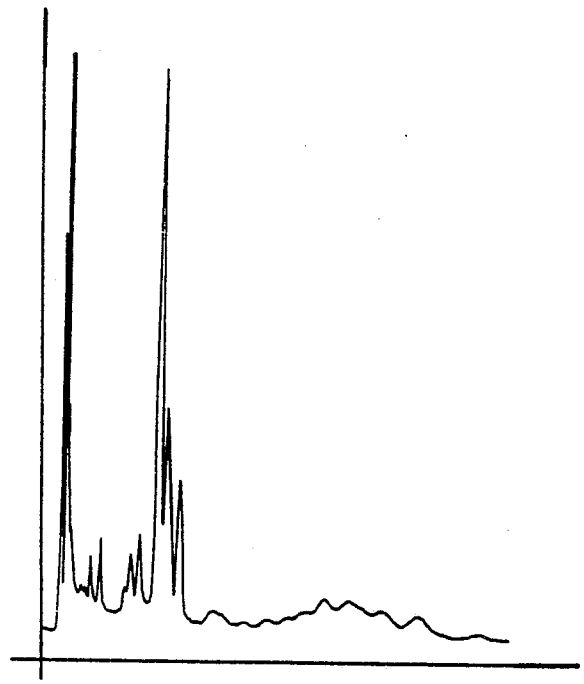

FIG. 37 is the GLC profile for the reaction product of Example IV(M).

Figure 38A:
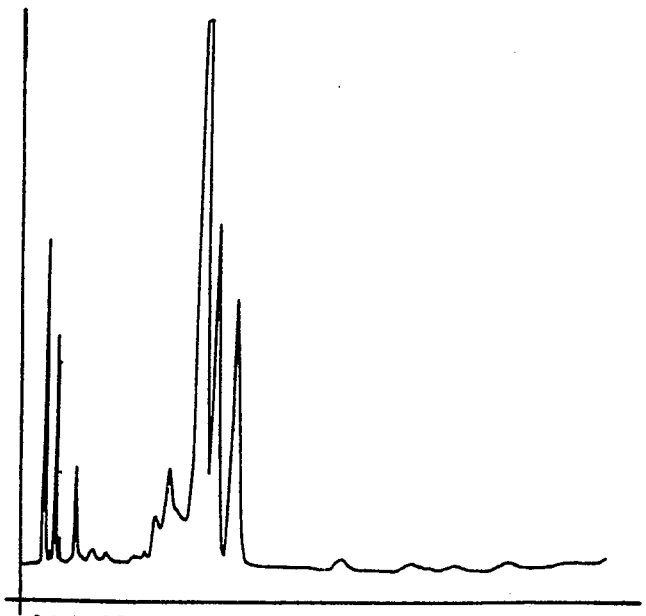

FIG. 38A is the GLC profile for the reaction product of Example V (conditions: barium hydroxide catalyst; methanol solvent; temperature: 70° C.; dimerization product of reaction product of isobutyraldehyde and acetone).

Figure 38B:
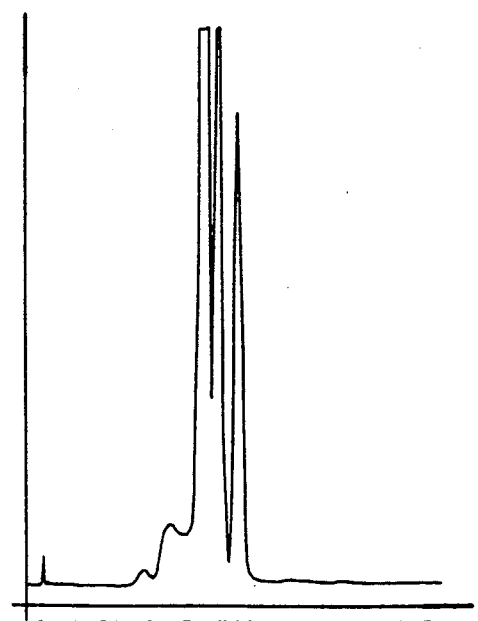

FIG. 38B is the GLC profile for bulked fractions 8–15 of the distillation product of the reaction product of Example V.

Figure 39A:
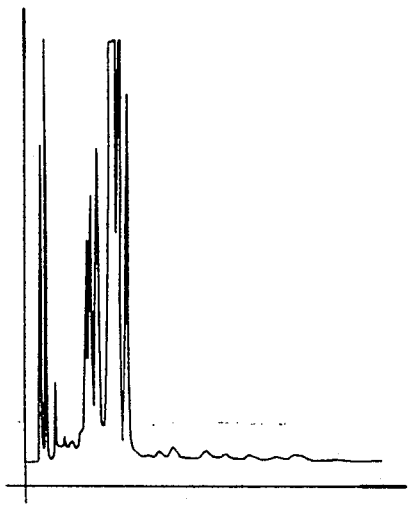

FIG. 39A is the GLC profile for the reaction product (after 2 hours) of Example VI (conditions: KOH catalyst; methanol solvent; reaction temperature: 50° C.; dimerization product of reaction product of isobutyraldehyde and acetone).

Figure 39B:
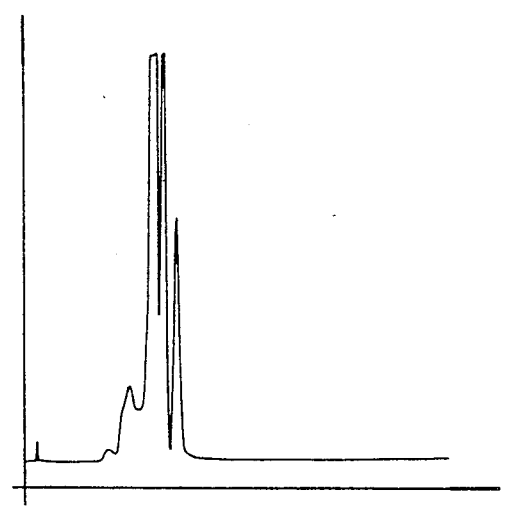

FIG. 39B is the GLC profile for bulked fractions 7–20 of the distillation product of the reaction product of Example VI.

Figure 40A:
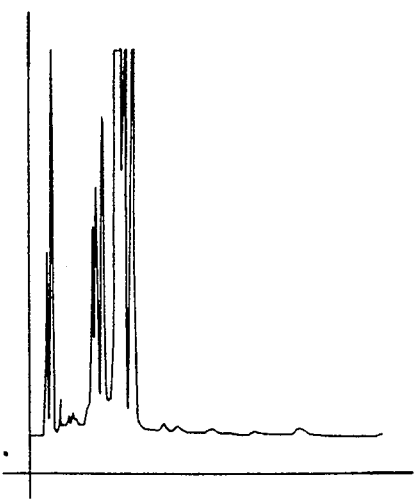

FIG. 40A is the GLC profile for the reaction product of Example VII (conditions: sodium hydroxide catalyst; methanol solvent; reaction temperature: 30° C.; dimerization product of reaction product of isobutyraldehyde and acetone).

Figure 40B:
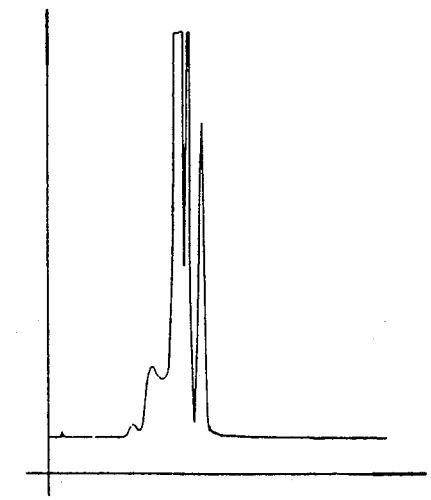

FIG. 40B is the GLC profile for bulked fractions 6–16 of the distillation product of the reaction product of Example VII.

DETAILED DESCRIPTION OF THE DRAWINGS

FIG. 4 is the GLC profile for the crude reaction product produced according to Example I.

The conditions are Carbowax column operated at 200° C., isothermal.

The Peak indicated by the reference numeral "1" is the starting material which is a mixture of compounds defined according to the structure:

wherein in the mixture in each of the molecules one of the dashed lines is a carbon-carbon double bond and the other of the dashed lines is a carbon-carbon single bond and the molecules are different.

The Peaks indicated by reference numerals "2", "3", "4", "5" and "6" represent products produced by means of the dimerization of the compound defined according to the structure:

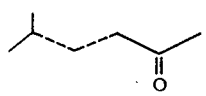

Thus, the Peak indicated by reference numeral "2" is "Peak 1" which is the compound having the structure:

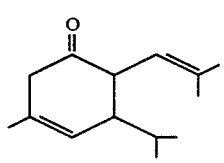

The Peak indicated according to reference numeral "3" is "Peak 2" having the structure:

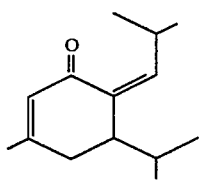

"Peak 3" indicated by reference numeral "4" has the structure:

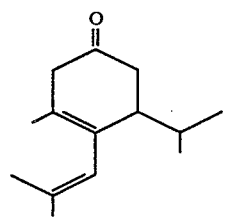

The Peak signified by reference numeral "5" is a combination of Peaks 4A and 4B. Peak 4A is the compound having the structure:

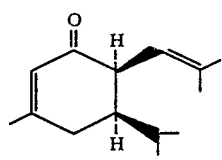

Peak 4B is either the compound having the structure:

Peak 4B is either the compound having the structure:

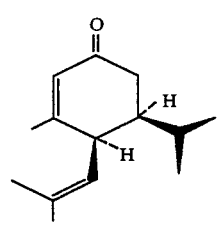

and/or the compound having the structure:

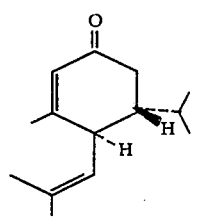

The Peak indicated by reference numeral "6" is Peak 5 which is the compound having the structure:

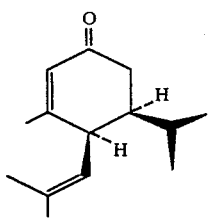

and/or the compound having the structure:

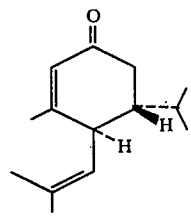

FIG. 5 is the GLC profile for bulked distillation fractions 11-19 of the distillation product of the reaction product of Example I.

The Peak indicated by reference numeral "7" is Peak 1 which is the compound having the structure:

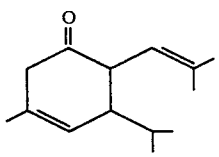

The Peak indicated by reference numeral "8" is Peak 2 having the structure:

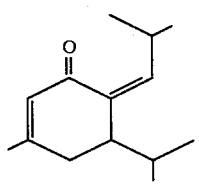

The Peak indicated by reference numeral "9" is Peak 3 having the structure:

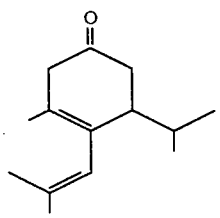

The Peak indicated by reference numeral "10" is Peak 4A having the structure:

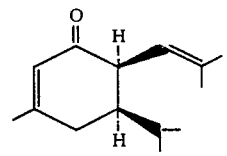

The Peak indicated by reference numeral "11" is Peak 4B having the structure:

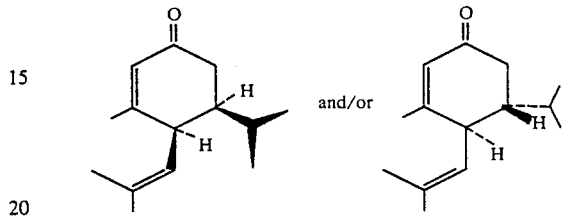

The Peak indicated by reference numeral "12" is Peak 5 having the structure:

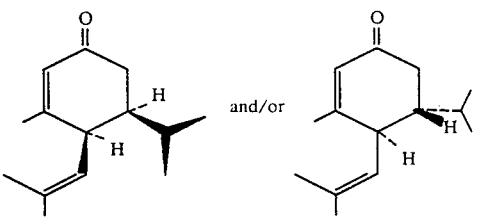

FIG. 18 is the GLC profile for bulked fractions 11-19 of the distillation product of the reaction product of Example I wherein the Peaks are grouped into three groupings:

Group "A" which is Peaks 1, 2 and 3 indicated by reference numerals "13", "14" and "15"

Group "B" which is Peak 4 indicated by reference numeral "17" and

Group "C" which is Peak 5 indicated by reference numeral "19".

In Group "A", the peak indicated by reference numeral "13" is Peak 1 having the structure:

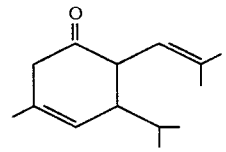

Peak 2 is indicated by reference numeral "14" and has the structure:

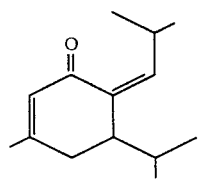

Peak 3 is indicated by reference numeral "15" and has the structure:

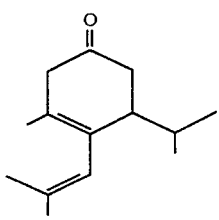

Peak 4 is indicated by reference numerals "17" and "18" and have the structures:

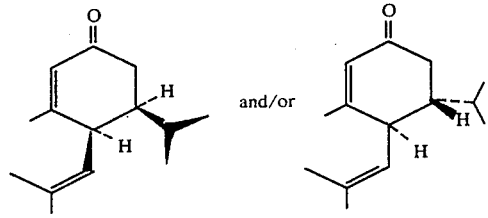

Peak 5 is indicated by reference numeral "19" and has the structure:

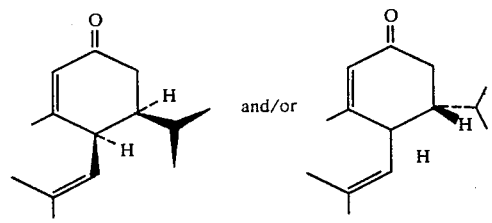

FIG. 20 is the GLC profile for the reaction product of Example III (conditions: SE-30 column programmed at 200° C., isothermal).

The Peak indicated by reference numeral "20" is Peak 1 having the structure:

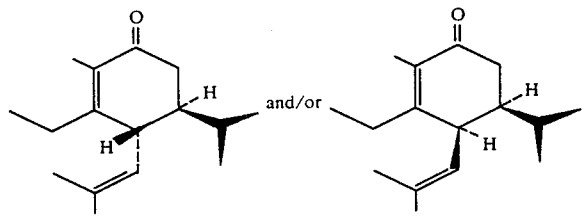

The Peak indicated by reference numeral "21" is Peak 2 having the structure:

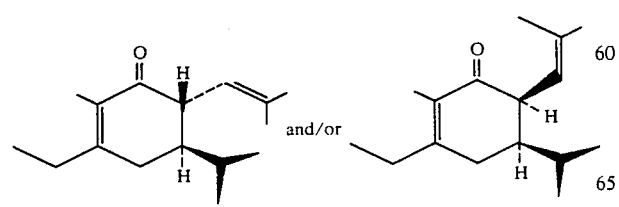

The Peak indicated by reference numeral "22" is Peak 3 having the structure:

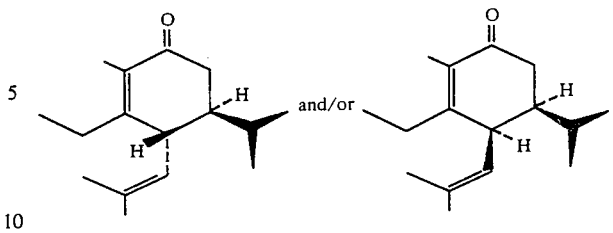

THE INVENTION

It has now been determined that certain substituted methyl isopropyl cyclohexenones defined according to the structure:

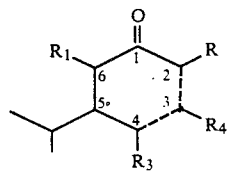

wherein one of the dashed lines represents a carbon-carbon double bond and the other of the dashed lines represents a carbon-carbon single bond; wherein $R_4$ represents methyl or ethyl; wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:

(i) when the dashed line at the 3-4 position is a double bond, then $R_3$ is hydrogen or 2-methyl-1-propenyl;

(ii) when the dashed line at the 2-3 position is a double bond, then $R_2$ is hydrogen or 2-methyl-1-propenyl;

(iii) when $R_4$ is ethyl, then $R_2$ is methyl and the double bond is at the 2-3 position; and (iv) when $R_4$ is methyl, then $R_2$ is hydrogen; 2-methyl-1-propenyl or 2-methyl-1-propylidenyl;

with the members of said genus being novel compounds when $R_4$ is ethyl or when $R_4$ is methyl and the double bond is at the 3-4 position or when $R_4$ is methyl and the double bond is at the 2-3 position with $R_3$ being hydrogen.

Briefly, our invention contemplates augmenting or enhancing the flavors and/or fragrances of such consumable materials as perfumes, perfumed articles, colognes, smoking tobaccos and smoking tobacco articles by adding thereto a small but effective amount of at least one of the compounds defined according to the structure:

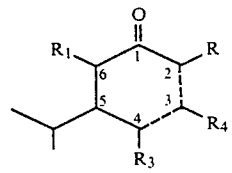

wherein the dashed lines and $R_1$, $R_2$, $R_3$ and $R_4$ are as defined supra.

Also contemplated within the scope of our invention are processes for preparing such compounds and the products produced by such processes. These processes involve the dimerization of the mixture of compounds defined according to the structure:

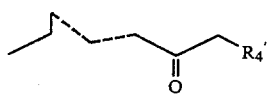

wherein $R_4'$ represents hydrogen or methyl and in the mixture one of the dashed lines is a carbon-carbon double bond and the other of the dashed lines is a carbon-carbon single bond, using a catalyst which is either an alkali metal hydroxide, an alkaline earth metal hydroxide, aluminum chloride, sulfuric acid, or pyrrolidinium acetate in the presence of an inert solvent such as ethanol, methanol, isopropanol, n-propanol, n-hexane, or toluene. The process can be carried out by producing the compounds defined according to the structure:

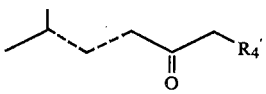

in situ by carrying out the aldol condensation of isobutyraldehyde having the structure:

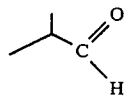

with the ketone having the structure:

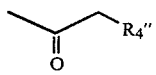

wherein $R_4''$ is hydrogen or methyl using the same solvent system as defined above and the same catalyst range as defined above.

The substituted methyl isopropyl cyclohexenone derivatives of our invention augment or enhance peppery, sweaty, guiacwood-like, green, burnt grass-like, vetiver-like, sandalwood-like, fresh, floral, citrusy and spicy aromas with sauge sclaree topnotes and musky undertones insofar as augmenting or enhancing the aroma of perfumes, perfumed articles and colognes of our invention.

The substituted methyl isopropyl cyclohexenones of our invention also augment or enhance, prior to smoking, the woody, peppery and citrusy aroma and taste nuances of smoking tobacco and smoking tobacco article components and, on smoking, impart a sweet, citrusy character to smoke flavor in smoking tobaccos and components of smoking tobacco articles in the main stream and in the side stream.

As stated supra, the reaction of our invention may be carried out by either (a) dimerization of the ketone mixture defined according to the structure:

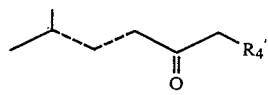

wherein in the mixture, one of the dashed lines represents a carbon-carbon double bond and the other of the dashed lines represents a carbon-carbon single bond and $R_4'$ represents hydrogen or methyl or (b) by forming the mixture of ketones defined according to the structure:

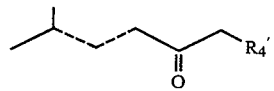

in situ by carrying out the reaction of isobutyraldehyde with the ketone defined according to the structure:

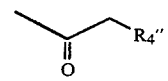

When carrying out the aforementioned reaction "in situ", this reaction can be shown thusly:

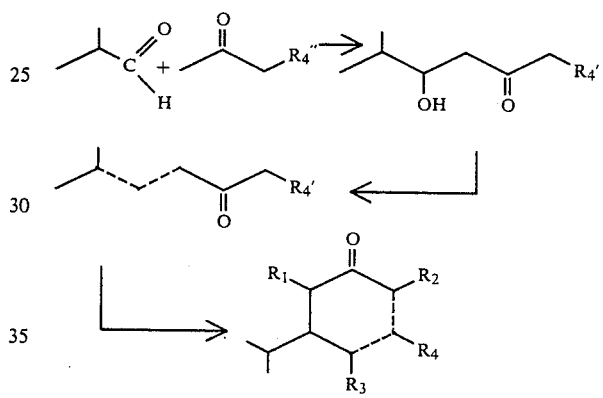

wherein $R_1$, $R_2$, $R_3$, $R_4$, $R_4'$, $R_4''$ and the dashed lines are defined as above.

Whether carrying out the reaction in situ or carrying out the dimerization starting with the ketone mixture defined according to the structure:

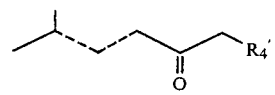

the reaction is carried out at a temperature in the range of from about 25° C. up to about 120° C. at atmospheric pressure in the presence of:

(a) a solvent which can be a hydrocarbon such as n-hexane or toluene; an inert alkanol such as methyl alcohol, ethyl alcohol or isopropyl alcohol; and (b) a catalyst which is either acidic or basic such as an alkali metal hydroxide such as potassium hydroxide or sodium hydroxide; an alkaline earth metal hydroxide such as barium hydroxide; aluminum chloride; or an amphoteric catalyst such as pyrrolidinium acetate defined according to the structure:

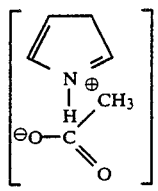

As will be seen by an examination of the GLC profiles in the figures as summarized supra, the isomer ratios of the reaction product mixture defined according to the structure:

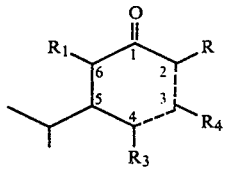

will vary and depend upon the following reaction variables:
(a) temperature of reaction;
(b) time of reaction;
(c) nature of catalyst;
(d) concentration of catalyst;
(e) nature of solvent;
(f) concentration of reactant in solvent;
(g) ratio of catalyst to reactant.

When carrying out the reaction between the isobutyraldehyde and ketone defined according to the structure:

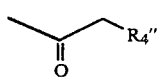

in situ, the mole ratio of isobutyraldehyde:ketone having the structure:

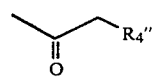

may vary from 1.5:0.5 up to 0.5:1.5 of isobutyraldehyde:ketone. The reaction temperature range may vary from about 25° C. up to about 120° C. and is preferably the temperature at which the reaction mass will reflux at atmospheric pressure. Thus, when carrying out the reaction using a methyl alcohol catalyst wherein the reactant concentration is 4 kg. per liter using methanol, the reaction temperature is maintained at 50°–52° C.

The concentration of catalyst in the reaction mass may vary from about 50 grams per liter up to about 400 grams per liter. The nature of the solvent may vary as set forth above with the preferred solvents being methanol, ethanol and isopropyl alcohol. The nature of the catalyst may vary as set forth above with the preferred catalysts being sodium hydroxide, potassium hydroxide and barium hydroxide.

Certain of the substituted methyl isopropyl cyclohexenones of our invention are novel compounds per se and these are defined according to the structure:

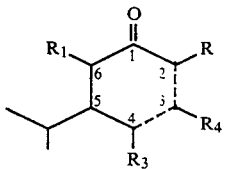

wherein one of the dashed lines represents a carbon-carbon double bond and the other of the dashed lines represents a carbon-carbon single bond; wherein $R_4$ represents methyl or ethyl; wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:

(i) when the dashed line at the 3-4 position is a double bond, then $R_3$ is hydrogen or 2-methyl-1-propenyl;

(ii) when the dashed line at the 2-3 position is a double bond, then $R_2$ is hydrogen or 2-methyl-1-propenyl;

(iii) when $R_4$ is ethyl, then $R_2$ is methyl and the double bond is at the 2-3 position; and (iv) when $R_4$ is methyl, then $R_2$ is hydrogen; 2-methyl-1-propenyl or 2-methyl-1-propylidenyl;

with the members of said genus being novel compounds when $R_4$ is ethyl or when $R_4$ is methyl and the double bond is at the 3-4 position or when $R_4$ is methyl and the double bond is at the 2-3 position with $R_3$ being hydrogen. Thus, for example, the compounds defined according to the structures:

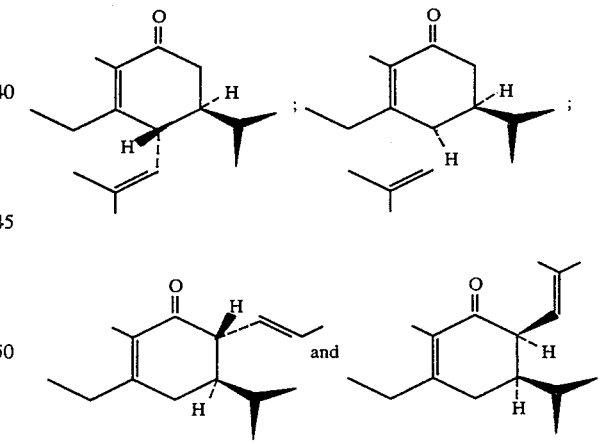

are novel compounds. On the other hand, the compounds defined according to the structures:

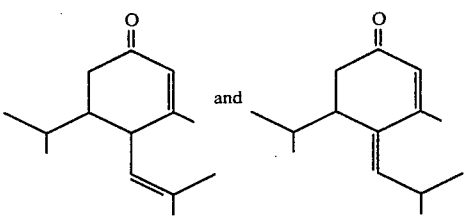

are the only compounds of the genus:

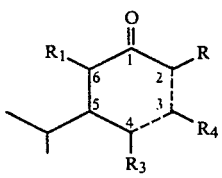

which are not novel.

The substituted methyl isopropyl cyclohexenones of our invention can be obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the substituted methyl isopropyl cyclohexenone derivatives of our invention by fractional distillation in vacuo.

The substituted methyl isopropyl cyclohexenone derivatives of our invention can be used alone or in combination to contribute peppery, sweaty, guiacwood-like, green, burnt grass, vetiver-like, sandalwood-like, fresh, floral, citrusy and spicy aroma nuances with sauge sclaree topnotes and musky undertones to perfumes, perfumed articles and colognes.

As olfactory agents, the substituted methyl isopropyl cyclohexenones of our invention can be formulated into or used as components of a "perfume composition" or can be used as components of a "perfumed article" or the perfume composition may be added to "perfumed articles".

The term "perfume composition" is used herein to mean a mixture of organic compounds including, for example, alcohols, aldehydes, ketones (other than the ketones of our invention), nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, the individual component will contribute its particular olfactory characteristics, but the overall effect of the perfume composition will be the sum total of the effects of each of the ingredients and possibly even more than the sum total of each of the effects of each of the ingredients if there exists synergism amongst the ingredients. Thus, the individual compounds of this invention or mixtures thereof can be used to alter, augment or enhance the aroma characteristics of a perfume composition, for example, by highlighting or moderating the olfactory reaction contributed by another ingredient in the composition.

The amount of the substituted methyl isopropyl cyclohexenone derivatives of this invention which will be effective in perfume compositions depends on many factors, including the other ingredients, their amounts and the effects which are desired. It has been found that perfume compositions containing as little as 0.05% of the methyl isopropyl cyclohexenone derivatives of this invention, or even less, can be used to impart an interesting peppery, sweaty, guiacwood-like, green, burnt grass-like, vetiver-like, sandalwood-like, fresh, floral, citrusy and/or spicy aroma profile with sauge sclaree topnotes and musky undertones to soaps, liquid and solid cationic, anionic, noionic and zwitterionic detergents, cosmetic powders, liquid and solid fabric softeners, fabric softener articles, optical brightener compositions and other products. The amount employed can range up to 50% or higher and will depend on considerations of cost, nature of the end product and the effect desired on the finished product and particular fragrance sought.

The substituted methyl isopropyl cyclohexenone derivatives of this invention can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powder such as talcs, dusting powders, face powders and the like. When used as an olfactory component of a perfumed article, as little as 0.01% of one or more of the substituted methyl isopropyl cyclohexenone derivatives of our invention will suffice to impart an interesting peppery, sweaty, guiacwood-like, green, burnt grass-like, vetiver-like, sandalwood-like, fresh, floral, citrusy and/or spicy aroma with sauge sclaree topnotes and musky undertones. Generally, no more than 0.5% (by weight of the perfumed article) is required. Thus, the range of use of the substituted methyl isopropyl cyclohexenones of our invention in perfumed articles is 0.01% up to 0.5% and the use in perfume compositions per se is from 0.05% up to 50% of the methyl isopropyl cyclohexenones of our invention.

In addition, the perfume composition can contain a vehicle or carrier for the substituted methyl isopropyl cyclohexenones of our invention taken alone or taken together with other ingredients. The vehicle can be a liquid such as an alcohol such as ethanol, a glycol such as propylene glycol or the like. The carrier can be an absorbent solid such as a gum (e.g. gum arabic or guar gum or xanthan gum) or components for encapsulating the composition such as gelatin (as by coacervation) which can be used to form a capsule wall surrounding the perfume oil, or a urea formaldehyde resin which is formed by polymerization to form a capsule wall surrounding the perfume oil.

An additional aspect of our invention provides an organoleptically improved smoking tobacco product and additives therefor including methods of making the same which overcome problems heretofore encountered in the creation or enhancement of specific desired woody, peppery and citrusy notes prior to smoking or sweet, citrusy notes on smoking both in the main stream and in the side stream. Such notes both prior to and on smoking in both the main stream and the side stream may now be readily controlled and maintained at the desired uniform level regardless of variations in the tobacco components of the blend; or the nature of the filter used in conjunction with the smoking tobacco article.

This invention further provides improved tobacco additives and additives for materials used in fabrication of tobacco articles (particularly smoking tobacco articles) and methods whereby desirable woody, peppery and citrusy notes prior to smoking and sweet, citrusy notes on smoking may be imparted to smoking tobacco compositions and smoking tobacco products and may be readily varied and controlled to produce the desired uniform flavor and characteristics.

In carrying out this aspect of our invention, we add to smoking tobacco materials or a suitable substitute therefor (e.g. dried lettuce leaves) an aroma and flavor additive containing as an active ingredient one or more of the substituted methyl isopropyl cyclohexenone derivatives of our invention.

In addition to the substituted methyl isopropyl cyclohexenones of our invention, other flavoring and aroma additives may be added to the smoking tobacco material or substitute therefor either separately or in admixture with one or more of the substituted methyl isopropyl cyclohexenone derivatives of our invention thusly:

I. Synthetic materials
  Beta-methylcinnamaldehyde
  Eugenol;
  Dipentene;
  Damascenone;
  Maltol;
  Ethyl maltol;
  Delta-undecalactone;
  Delta-decalactone;
  Benzaldehyde;
  Amyl acetate;
  Ethyl butyrate;
  Ethyl valerate;
  Ethyl acetate
  2-hexen-1-ol;
  2-methyl-5-isopropyl-1,3-nonadiene-8-one;
  2-methyl-5-isopropylacetophenone;
  2-hydroxy-2,5,5,8α-tetramethyl-1-(2-hydroxyethyl)-decahydronaphthalene;
  Dodecahydro-3α,6,6,9α-tetramethylnaphthol (2,1-β-furan;
  4-hydroxyhexenoic acid, gamma-lactone;
  Polyisoprenoid hydrocarbons defined in Example V of U.S. Pat. No. 3,589,372 issued on June 29, 1971
II. Natural Oils
  Celery seed oil;
  Coffee extract;
  Bergamot oil;
  Cocoa extract;
  Nutmeg oil;
  Origanum oil.

An aroma and flavoring concentrate containing one or more of the substituted methyl isopropyl cyclohexenone derivatives of our invention and, if desired, one or more of the above indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste, but insofar as enhancement of the imparting of woody, peppery and/or citrusy and sweet notes prior to and on smoking in both the main stream and the side stream, we have found that satisfactory results are obtained if the proportion by weight of the sum total of the substituted methyl isopropyl cyclohexenones to smoking tobacco material is between 50 ppm and 2,500 ppm (0.005%–0.25%) of the active ingredients to the smoking tobacco material. We have further found that satisfactory results are obtained if the proportions by weight of the sum total of substituted methyl isopropyl cyclohexenone derivatives used to flavoring material is between 0.05:1 and 0.50:1.

Any convenient method for incorporating the substituted methyl isopropyl cyclohexenone derivatives in the tobacco product may be employed. Thus, the substituted methyl isopropyl cyclohexenone derivatives taken alone or along with other flavoring additives may be dissolved in a suitable solvent such as food grade ethanol, pentane, diethyl ether and/or other volatile organic solvents and the resulting solution may either be sprayed on the cured, cased and blended tobacco material; or the tobacco material or filter may be dipped into such solution. Under certain circumstances, a solution of one or more substituted methyl isopropyl cyclohexenone derivatives taken alone or taken further together with other flavoring additives as set forth above may be applied by means of a suitable applicator such as a brush or roller on the paper or leaf wrapper for the smoking product or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more substituted methyl isopropyl cyclohexenone derivatives of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, the substituted methyl isopropyl cyclohexenone derivatives of our invention can be incorporated with material such as filter tip materials, seam paste, packaging materials and the like which are used along with the tobacco to form a product adapted for smoking. Further, the substituted methyl isopropyl cyclohexenone derivatives of our invention can be added to certain tobacco substitutes of natural or synthetic origin (e.g. dried lettuce leaves) and, accordingly, by the term "tobacco" as used throughout this specification is meant any composition intended for human consumption by smoking or otherwise, whether composed of tobacco plant parts or substitute material or both.

It will thus be apparent that the substituted methyl isopropyl cyclohexenone derivatives of our invention can be utilized to alter, modify, augment or enhance sensory properties, particularly organoleptic properties such as flavors and/or fragrances of a wide variety of consumable materials.

The following Example A serves to illustrate a method for producing a precursor for producing the products of our invention (an aldol condensate). The following Examples I–IV inclusive, serve to illustrate the processes for carrying out the chemical syntheses of the products of our invention. The following Examples V et seq. set forth the uses of the products of Examples I–IV of our invention. The invention is to be considered restricted to these examples only as indicated in the appended claims.

All parts and percentages given herein are by weight unless otherwise specified.

EXAMPLE A

PREPARATION OF 5-METHYL-HEXENE-2-ONE MIXTURE

Reaction

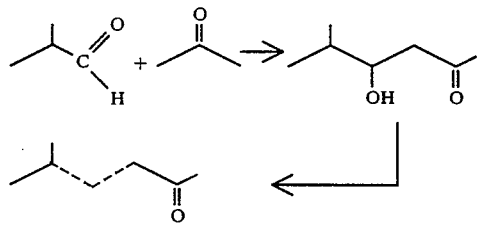

Into a 5 liter reaction flask equipped with stirrer, thermometer, condenser, addition funnel and heating mantle and fitted with a Soxhlet apparatus containing a thimble filled with barium hydroxide (200 grams) is placed a mixture of 1.5 kg of isobutyraldehyde and 1.4 kg of acetone.

The reaction mass is refluxed and the resultant 5-methylhexene-2-one mixture is collected in the reaction flask for a period of 4 hours.

At the end of the 4 hour period, the reaction mass is stripped of excess reactants and 2.3 kg of 5-methyl-hexene-2-one compounds are collected via distillation at a temperature of 74° C. and a pressure of 0.8 mm/Hg pressure.

Figure 1:
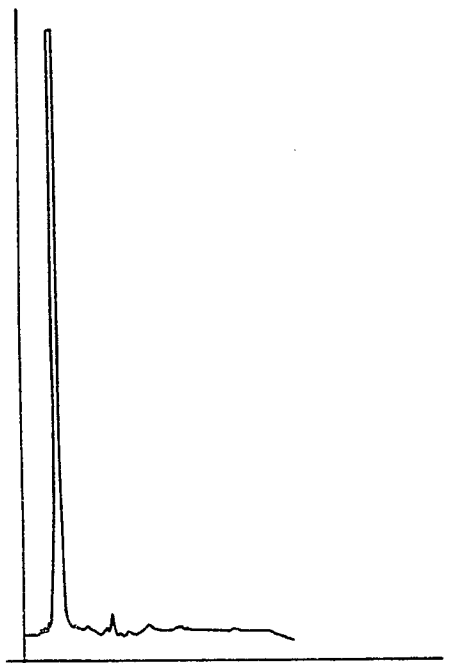
FIG. 1 is the GLC profile for the reaction product of Example A wherein the mixture defined according to the structure.

FIG. 1 is the GLC profile of the reaction product (conditions: Carbowax column operated at 200° C. isothermal).

FIG. 2 is the NMR spectrum for the reaction product collected via distillation at the temperature of 74° C. and 0.8 mm/Hg pressure.

FIG. 3 is the infra-red spectrum for the resulting product which is a mixture of compounds defined according to the structure:

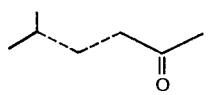

wherein in the mixture, in each of the molecules, one of the dashed lines is a carbon-carbon double bond and the other of the dashed lines is a carbon-carbon single bond and the molecules of the mixture are different.

EXAMPLE I

DIMERIZATION OF 5-METHYL-HEXENE-2-ONE MIXTURE

Reaction

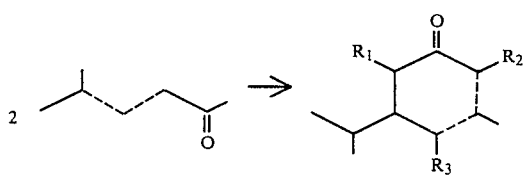

wherein one of $R_1$, $R_2$ or $R_3$ is 2-methyl-1-propenyl having the structure:

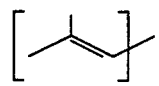

or 2-methyl-1-propylidenyl having the structure:

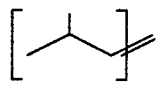

and the other two of $R_1$, $R_2$ or $R_3$ is hydrogen; and wherein in the mixture, in each of the molecules of the mixture, one of the dashed lines is a carbon-carbon double bond and the other of the dashed lines is a carbon-carbon single bond and wherein the molecules of the mixture are represented thusly:

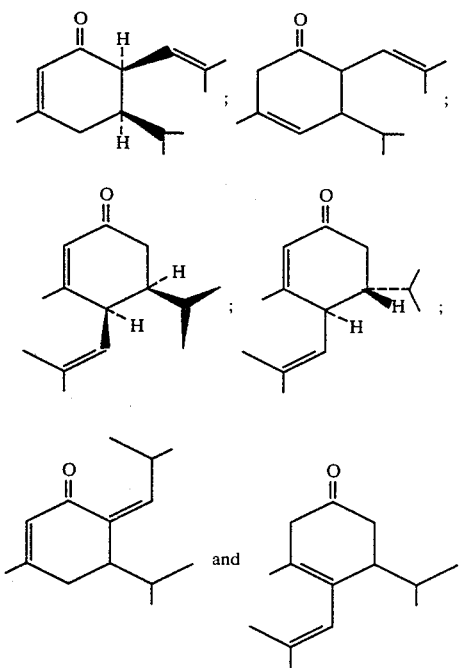

Into a 5 liter reaction flask equipped with stirrer, thermometer, condenser, addition funnel, heating mantle, cooling bath and Therm-o-watch apparatus is placed 100 grams of potassium hydroxide. 500 ml of methanol is placed in an addition funnel. Over a period of 10 minutes, the methanol is added to the KOH. After the methanol is mixed with the KOH, the resulting mixture is heated to 50° C. and over a period of 1 hour, the 5-methyl-hexene-2-one mixture (2 kg) produced according to Example A (boiling point 74° C. at 0.8 mm/Hg pressure) is added to the reaction mass while maintaining the reaction mass at 50°-55° C. At the end of the addition, the reaction mass is stirred for a period of 1.5 hours at 50°-51° C. The reaction mass is then added to two liters of water and the resulting organic layer is washed with two liters of water to a pH of 7. The organic layer is then distilled on a 24" Goodloe column to yield 917.2 grams of product and the fractions resulting from this distillation are as follows:

| Fraction Number | Vapor Temp. (°C.) | Liquid Temp. (°C.) | Pressure mm/Hg | Reflux Ratio | Weight of Fraction (grams) |
|---|---|---|---|---|---|
| 1 | 60/85 | 147/143 | 0.4/.25 | 9:1 | 47.2 |
| 2 | 92 | 140 | 0.25 | 9:1 | 44.5 |
| 3 | 98 | 140 | 0.30 | 9:1 | 36.3 |
| 4 | 84 | 139 | 0.22 | 9:1 | 44.7 |
| 5 | 88 | 141 | 0.40 | 9:1 | 39.9 |
| 6 | 88 | 142 | 0.40 | 9:1 | 42.0 |
| 7 | 88/95 | 140/141 | 0.4/0.4 | 9:1 | 41.0 |
| 8 | 104 | 145 | 0.7 | 9:1 | 45.7 |
| 9 | 101 | 148 | 0.6 | 9:1 | 43.1 |
| 10 | 103 | 148 | 0.5 | 9:1 | 39.9 |
| 11 | 102 | 148 | 0.4 | 9:1 | 48.2 |
| 12 | 102 | 148 | 0.4 | 9:1 | 49.8 |
| 13 | 103 | 149 | 0.4 | 9:1 | 41.2 |
| 14 | 104 | 150 | 0.4 | 9:1 | 24.8 |
| 15 | 103 | 150 | 0.4 | 9:1 | 47.0 |
| 16 | 92/100 | 145/147 | 0.4/0.4 | 2:1 | 36.4 |
| 17 | 93 | 142 | 0.4 | 2:1 | 48.7 |
| 18 | 93 | 143 | 0.4 | 2:1 | 41.6 |
| 19 | 93 | 146 | 0.4 | 2:1 | 45.1 |
| 20 | 93 | 150 | 0.4 | 2:1 | 38.1 |
| 21 | 95 | 195 | 0.5 | 2:1 | 39.6 |

Fractions 7–22 are bulked for the purposes of organoleptic evaluation. From an aroma standpoint, bulked fractions 7–22 have a peppery, guiacwood-like, vetiver-like, sandalwood-like aroma with a sauge sclaree topnote and a musky undertone.

FIG. 4 is the GLC profile for the crude reaction product (GLC conditions: Carbowax column operated at 200° C. isothermal).

The Peak on the GLC profile indicated by the reference numeral "1" represents the starting material having the structure:

a mixture, wherein in the mixture in one of the molecules one of the dashed lines is a carbon-carbon double bond and the other of the dashed lines is a carbon-carbon single bond and in the other of the molecules, the other of the dashed lines is a carbon-carbon double bond.

The Peak indicated by the reference numeral "2", Peak 1, has the structure:

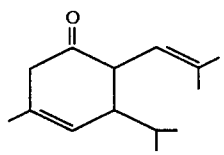

The Peak indicated by the reference numeral "3", Peak 2, has the structure:

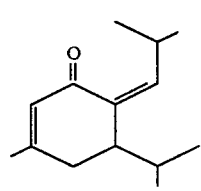

The Peak indicated by the reference numeral "4", Peak 3, has the structure:

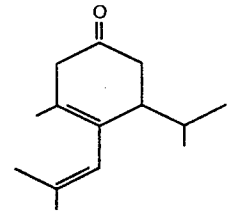

The Group of Peaks indicated by the reference numeral "5" is a mixture of Peaks 4A and 4B. Peak 4A has the structure:

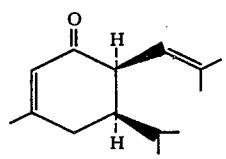

Peak 4B has the structure:

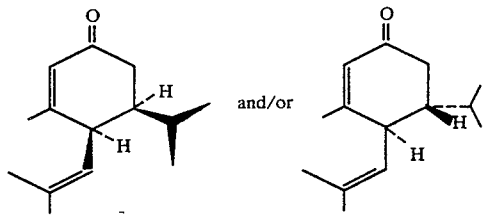

The Peak indicated by reference numeral "6" is Peak 5 and it has the structure:

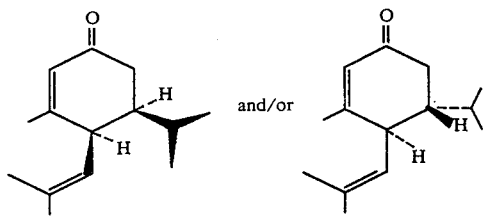

FIG. 5 is the GLC profile for the bulked distillation fractions 11–19 of the foregoing distillation of the foregoing reaction product.

The Peak indicated by reference numeral "7" is Peak 1 having the structure:

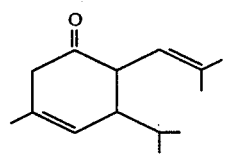

The Peak indicated by reference numeral "8" is Peak 2 having the structure:

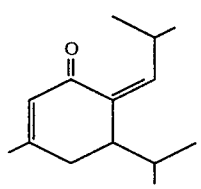

The Peak indicated by reference numeral "9" is Peak 3 having the structure:

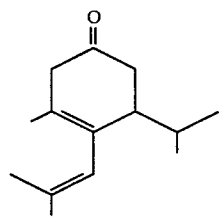

The Peak indicated by reference numeral "10" is Peak 4A having the structure:

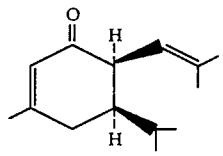

The Peak indicated by reference numeral "11" is Peak 4B having the structure:

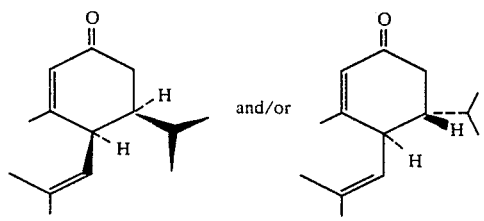 and/or

The Peak indicated by reference numeral "12" is Peak 5 having the structure:

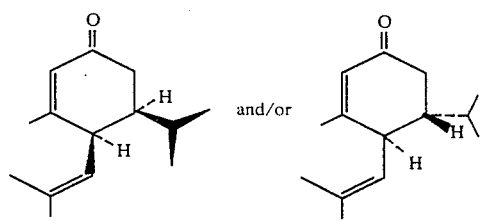 and/or

FIG. 6 is the NMR spectrum for Peak 1 having the structure:

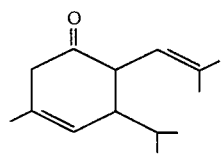

FIG. 7 is the IR spectrum for Peak 1 of the foregoing GLC profile having the structure:

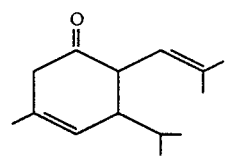

FIG. 8 is the NMR spectrum for Peak 2 of the foregoing GLC profile having the structure:

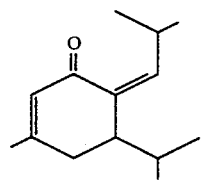

FIG. 9 is the infra-red spectrum for Peak 2 of the foregoing GLC profile having the structure:

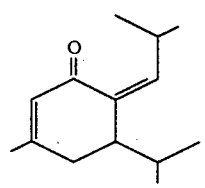

FIG. 10 is the NMR spectrum for Peak 3 of the foregoing GLC profile having the structure:

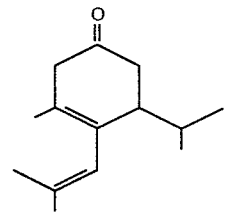

FIG. 11 is the infra-red spectrum for Peak 3 of the foregoing GLC profile having the structure:

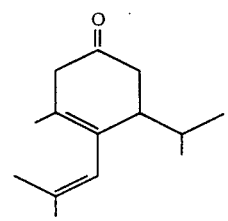

FIG. 12 is the NMR spectrum for Peak 4A of the foregoing GLC profile having the structure:

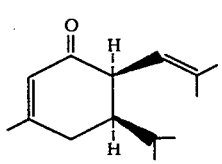

FIG. 13 is the infra-red spectrum for Peak 4A of the foregoing GLC profile having the structure:

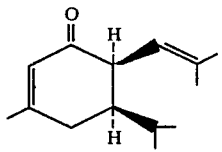

FIG. 14 is the NMR spectrum for Peak 4B of the foregoing GLC profile having the structure:

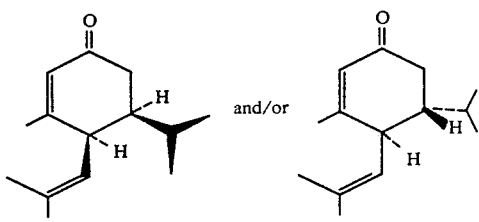

FIG. 15 is the infra-red spectrum for Peak 4B of the foregoing GLC profile having the structure:

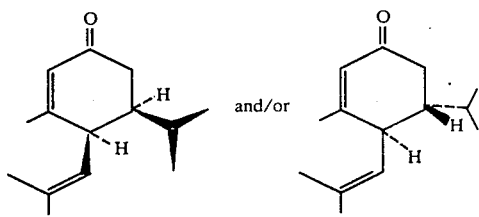

FIG. 16 is the NMR spectrum for Peak 5 of the foregoing GLC profile having the structure:

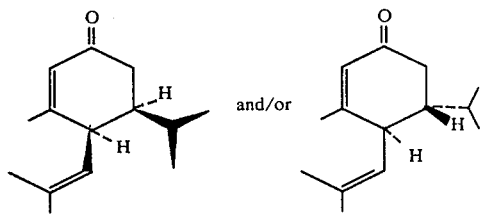

FIG. 17 is the infra-red spectrum for Peak 5 of the foregoing GLC profile having the structure:

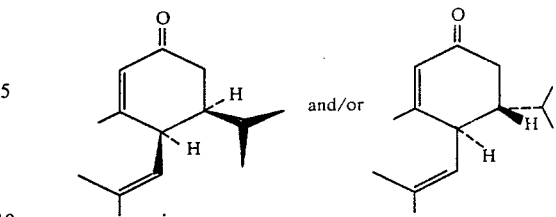

FIG. 18 is the GLC profile for bulked fractions 11–19.

The Peaks of the GLC profile are grouped as follows:
Group "A" is a mixture of Peaks 1, 2 and 3. Group "A" has a sweaty, burnt grass aroma.

Group "B" is a mixture of Peaks 4A and 4B. Group "B" has an intense peppery, guiacwood, vetiver, sandalwood-like aroma with a sauge sclaree top-note and a musky undertone.

Group "C" is Peak 5. Group "C" has a green, vetiver aroma.

EXAMPLE II

PREPARATION OF SUBSTITUTED METHYL ISOPROPYL CYCLOHEXENONE MIXTURE

Reaction

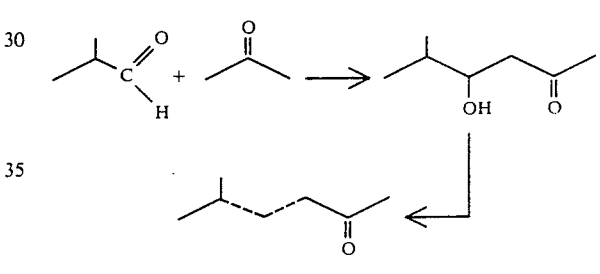

and

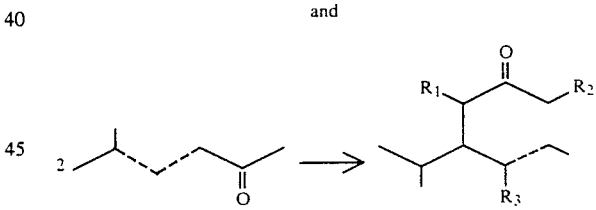

wherein one of the dashed lines represents a carbon-carbon double bond and the other of the dashed lines represents a carbon-carbon single bond and wherein one of $R_1$, $R_2$ and $R_3$ is 2-methyl-1-isopropylidenyl having the structure:

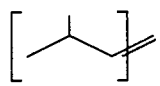

or 2-methyl-1-isopropenyl having the structure:

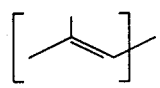

and the other of $R_1$, $R_2$ and $R_3$ represents hydrogen in each of the components of the mixture.

Into a 12 liter reaction flask equipped with stirrer, thermometer, reflux condenser, dropping funnel, heating mantle and cooling bath is placed 1,160 grams of acetone, 250 grams of potassium hydroxide and 1,000 ml of anhydrous methyl alcohol. The reaction mass is heated to 50° C. and while maintaining the reaction mass at 50°-52° C., over a period of 1 hour is placed 1 kg of isobutyraldehyde. The reaction mass is then heated for a period of 2 hours at 52° C. At the end of the reaction, the reaction mass is poured into two liters of 10% salt solution. The resulting aqueous mixture is washed with 1 liter of toluene. The toluene extract is then washed with three 1-liter portions of water to a pH of 7. The resulting reaction product is evaporated and then distilled yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 55/71 | 125/127 | 1.0/1.0 | 9:1/9:1 | 24.2 |
| 2 | 73 | 124 | 1.0 | 9:1 | 33.2 |
| 3 | 74 | 125 | 0.8 | 9:1 | 33.0 |
| 4 | 87 | 125 | 0.8 | 9:1 | 43.9 |
| 5 | 91 | 126 | 0.8 | 9:1 | 23.7 |
| 6 | 95 | 130 | 0.8 | 100% | 43.5 |
| 7 | 95 | 130 | 0.8 | 100% | 43.4 |
| 8 | 95 | 132 | 0.8 | 100% | 45.4 |
| 9 | 95 | 132 | 0.8 | 100% | 51.3 |
| 10 | 95 | 133 | 0.8 | 100% | 43.1 |
| 11 | 95 | 133 | 0.8 | 100% | 42.9 |
| 12 | 95 | 133 | 0.8 | 100% | 41.0 |
| 13 | 97 | 134 | 0.8 | 100% | 38.5 |
| 14 | 97 | 134 | 0.8 | 100% | 43.6 |
| 15 | 97 | 135 | 0.8 | 100% | 44.9 |
| 16 | 97 | 137 | 0.8 | 100% | 43.8 |
| 17 | 97 | 138 | 0.8 | 100% | 44.2 |
| 18 | 97 | 142 | 0.8 | 100% | 44.6 |
| 19 | 97 | 146 | 0.8 | 100% | 46.6 |
| 20 | 100 | 162 | 0.8 | 100% | 39.8 |
| 21 | 100 | 167 | 0.8 | 100% | 8.0 |

Fractions 2-6 are bulked and evaluated as having a peppery, guiacwood-like, vetiver-like aroma with sauge sclaree topnotes.

FIG. 19A is the GLC profile of a reaction product subsequent to the reaction but prior to distillation.

FIG. 19B is the GLC profile of bulked fractions 7-17. It is bulked fractions 7-17 which have the peppery, guiacwood-like, vetiver aroma with the sauge sclaree topnotes.

EXAMPLE III

PREPARATION OF SUBSTITUTED METHYL ISOPROPYL CYCLOHEXENONE MIXTURE FROM METHYL ETHYL KETONE AND ISOBUTYRALDEHYDE

Reaction

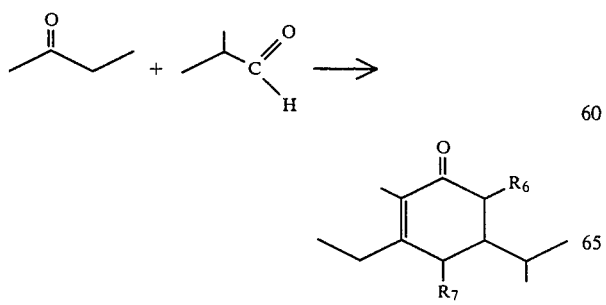

wherein one of $R_6$ and $R_7$ in the resulting mixture is 2-methyl-1-propenyl and the other of $R_6$ or $R_7$ in the mixture is hydrogen.

Into a 12 liter reaction flask equipped with thermometer, stirrer, addition funnel, reflux condenser and heating mantle is placed 1,000 ml methanol and 250 grams of potassium hydroxide. The resulting mixture is heated to 50° C. and over a five minute period, 1,200 grams of methyl ethyl ketone is added. While maintaining the reaction mixture at 50° C. over a period of 1 hour, 1,000 grams of isobutyraldehyde is added to the reaction mass. The reaction mass is then stirred at 50° C. for a period of 1.5 hours. At the end of the 1.5 hour period, the reaction mass is poured into 2,000 ml of water and extracted with 1 liter of toluene. The resulting toluene extract is washed with water to a pH of 6-7. The resulting material is then stripped of solvent and distilled in a Goodloe column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 35/217 | 112/127 | 2.4/2.4 | 17.8 |
| 2 | 78 | 137 | 1.4 | 43.9 |
| 3 | 104 | 147 | 1.0 | 44.1 |
| 4 | 108 | 148 | 1.0 | 40.0 |
| 5 | 111 | 150 | 0.8 | 45.5 |
| 6 | 111 | 150 | 0.7 | 43.9 |
| 7 | 112 | 150 | 1.0 | 44.4 |
| 8 | 108 | 150 | 0.5 | 45.1 |
| 9 | 108 | 150 | 0.4 | 46.6 |
| 10 | 107 | 149 | 0.5 | 57.1 |
| 11 | 105 | 148 | 0.4 | 45.8 |
| 12 | 104 | 147 | 0.4 | 46.4 |
| 13 | 103 | 147 | 0.4 | 46.7 |
| 14 | 103 | 149 | 0.4 | 47.4 |
| 15 | 105 | 151 | 0.4 | 47.7 |
| 16 | 108 | 154 | 0.6 | 47.4 |
| 17 | 105 | 154 | 0.4 | 46.2 |
| 18 | 107 | 155 | 0.6 | 47.7 |
| 19 | 112 | 165 | 0.6 | 52.5 |
| 20 | 113 | 167 | 0.4 | 46.9 |
| 21 | 120 | 176 | 0.4 | 42.7 |
| 22 | 124 | 182 | 0.4 | 41.2 |
| 23 | 128 | 191 | 0.6 | 31.0 |
| 24 | 135 | 250 | 0.5 | 30.5 |

Fractions 4-18 of the foregoing distillation fractions are bulked and evaluated from an organoleptic standpoint. Bulked fractions 4-18 have a fresh, floral, citrus and spicy aroma.

FIG. 20 is the GLC profile of the reaction product prior to distillation.

Peak 1 or Peak 3 have the structures:

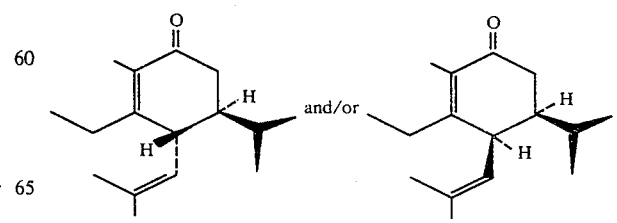

Peak 2 has the structures:

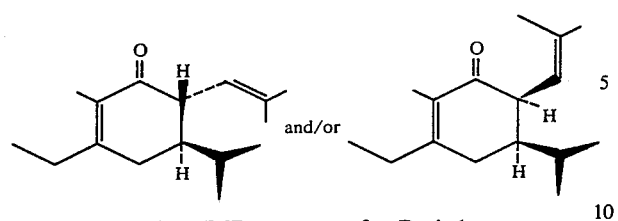

and/or

FIG. 21 is the NMR spectrum for Peak 1.
FIG. 22 is the IR spectrum for Peak 1 of the foregoing GLC profile.
FIG. 23 is the NMR spectrum for Peak 2 of the foregoing GLC profile.
FIG. 24 is the infra-red spectrum for Peak 2 of the foregoing GLC profile.
FIG. 25 is the NMR spectrum for Peak 3 of the foregoing GLC profile.
FIG. 26 is the infra-red spectrum for Peak 3 of the foregoing GLC profile.

EXAMPLES IV(A-M)

PREPARATION OF SUBSTITUTED METHYL ISOPROPYL CYCLOHEXENONE MIXTURES USING VARIOUS CATALYSTS AND VARIOUS SOLVENTS

Reaction

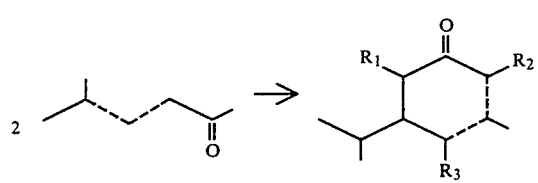

wherein one of $R_1$, $R_2$ and $R_3$ is hydrogen and the other of $R_1$, $R_2$ or $R_3$ is 2-methyl-1-propylidene or 2-methyl-1-propenyl having the structures, respectively:

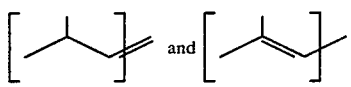

and wherein one of the dashed lines represents a carbon-carbon double bond and where the other of the dashed lines represents a carbon-carbon single bond.

The following Table I summarizes the reaction conditions for the general reaction procedure set forth below:

Into a 1 liter flask equipped with thermometer, stirrer, addition funnel, reflux condenser and heating mantle is placed 200 ml of solvent as specified in Table I below and 50 grams of catalyst as specified in Table I below. The resulting mixture is heated at a temperature as indicated in Table I below and to the mixture over a period of 10 minutes is added 250 grams of 5-methyl-hexene-2-one mixture prepared according to Example A (boiling point 74° C. at 0.8 mm/Hg). The resulting mixture is heated at a temperature as indicated in Table I below for a period of 1 hour at the end of which period of time the reaction mass is poured into 500 ml water. The organic phase is then washed with water to a pH of 6-7 and a GLC profile is run in order to ascertain the extent of product produced. In Table I set forth below, an indication is set forth whether product is produced or not. In each of the cases, the product produced is defined according to the generic structure:

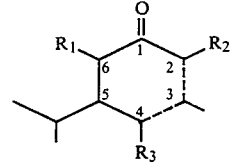

which is a mixture wherein in the mixture, one of $R_1$, $R_2$ and $R_3$ is 2-methyl-1-propenyl or 2-methyl-1-propylidenyl and the other of $R_1$, $R_2$ and $R_3$ is hydrogen and wherein one of the dashed lines represents a carbon-carbon double bond and the other of the dashed lines represents a carbon-carbon single bond.

TABLE I

| Example | Catalyst | Solvent | Temperature | Indication of Product Formed |
|---|---|---|---|---|
| IV(A) | sulfuric acid | toluene | 110° C. | No products produced |
| IV(B) | sodium hydroxide | ethyl alcohol | 50° C. | Product produced |
| IV(C) | potassium hydroxide | methyl alcohol | 65° C. | Product produced |
| IV(D) | barium hydroxide | ethyl alcohol | 78° C. | Product produced |
| IV(E) | aluminum chloride | n-hexane | 70° C. | Product produced |
| IV(F) | sulfuric acid | n-hexane | 70° C. | Product produced |
| IV(G) | sodium hydroxide | ethyl alcohol | 78° C. | Product produced |
| IV(H) | potassium hydroxide | ethyl alcohol | 78° C. | Product produced |
| IV(J) | potassium hydroxide | methyl alcohol | 30° C. | Product produced |
| IV(K) | sodium hydroxide | isopropyl alcohol | 82° C. | produced |
| IV(L) | barium hydroxide | isopropyl alcohol | 82° C. | Product produced |
| IV(M) | pyrrolidinium acetate having the structure: | methyl alcohol | 65° C. | Product produced |

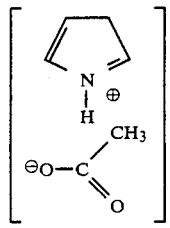

FIG. 27 is the GLC profile for Example IV(B).
FIG. 28 is the GLC profile for Example IV(C).
FIG. 29 is the GLC profile for Example IV(D).
FIG. 30 is the GLC profile for Example IV(E).
FIG. 31 is the GLC profile for Example IV(F).
FIG. 32 is the GLC profile for Example IV(G).
FIG. 33 is the GLC profile for Example IV(H).
FIG. 34 is the GLC profile for Example IV(J).
FIG. 35 is the GLC profile for Example IV(K).
FIG. 36 is the GLC profile for Example IV(L).
FIG. 37 is the GLC profile for Example IV(M).

EXAMPLE V

PREPARATION OF SUBSTITUTED METHYL ISOPROPYL CYCLOHEXENONE DERIVATIVE MIXTURE

Reaction

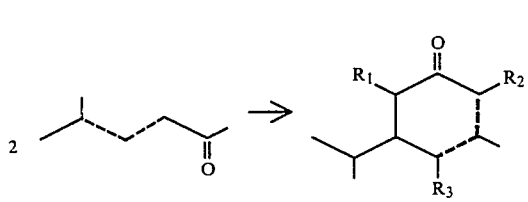

Into a 12 liter flask equipped with stirrer, thermometer, condenser, addition funnel and heating mantle is placed 250 grams of barium hydroxide and 200 ml methyl alcohol. The resulting mixture is heated to reflux and while refluxing over a period of 20 minutes 3 kg of 5-methyl-hexene-2-one mixture produced according to Example A is added slowly to the reaction mass. The reaction mass is refluxed for a period of 1.5 hours after which time the reaction mass is poured into 2000 ml of water. The organic phase is separated from the aqueous phase and the organic phase is washed with water to a pH of 6-7 and distilled on an 18" Goodloe column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 42/78 | 124/130 | 1.4/1.2 | 9.1/9.1 | 44.7 |
| 2 | 82 | 127 | 1.2 | 9.1 | 61.1 |
| 3 | 92 | 129 | 1.4 | 9.1 | 54.3 |
| 4 | 89 | 130 | 1.0 | 9.1 | 84.4 |
| 5 | 89 | 130 | 1.0 | 9.1 | 69.4 |
| 6 | 100 | 137 | 1.3 | 100% | 97.5 |
| 7 | 102 | 138 | 1.2 | 100% | 82.2 |
| 8 | 104 | 138 | 1.2 | 100% | 98.5 |
| 9 | 105 | 140 | 1.2 | 100% | 104.7 |
| 10 | 105 | 142 | 1.2 | 100% | 103.0 |
| 11 | 105 | 142 | 1.2 | 100% | 110.0 |
| 12 | 107 | 142 | 1.2 | 100% | 80.6 |
| 13 | 105 | 142 | 1.2 | 100% | 83.1 |
| 14 | 107 | 144 | 1.2 | 100% | 98.9 |
| 15 | 109 | 145 | 1.2 | 100% | 80.7 |
| 16 | 109 | 147 | 1.2 | 100% | 75.2 |
| 17 | 109 | 147 | 1.6 | 100% | 73.0 |
| 18 | 108 | 167 | 1.6 | 100% | 73.9 |

The resulting product has an excellent peppery, guiacwood, vetiver aroma with sauge sclaree topnotes.

FIG. 38A is the GLC profile of the reaction mass prior to distillation.

FIG. 38B is the GLC profile for bulked fractions 8-15 which is the bulking responsible for the foregoing organoleptic evaluation.

EXAMPLE VI

PREPARATION OF SUBSTITUTED METHYL ISOPROPYL CYCLOHEXENONE DERIVATIVE MIXTURE

Reaction

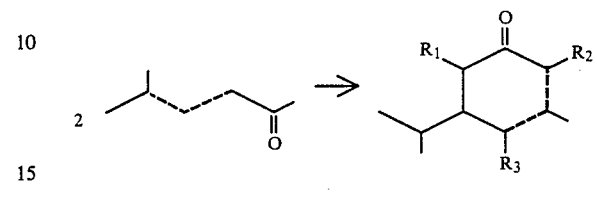

Into a 12 liter reaction flask equipped with thermometer, stirrer, addition funnel, reflux condenser and heating mantle is placed 250 grams of potassium hydroxide and 200 ml methanol. The mixture is heated to 50° C. and while maintaining the temperature at 50° C. over a period of 30 minutes, 3 kg of 5-methyl-hexene-2-one prepared according to Example A is added to the reaction mixture. The reaction mixture is heated to 50° C. for a period of 1.4 hours after which time the reaction mass is poured into 2000 ml water. The aqueous phase is separated from the organic phase and the organic phase is washed with water to a pH of 6-7 and then distilled yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 52/72 | 120/125 | 0.8/0.8 | 9:1/9:1 | 55.0 |
| 2 | 72 | 125 | 0.5 | 9:1 | 75.9 |
| 3 | 72 | 125 | 0.5 | 9:1 | 78.5 |
| 4 | 72 | 125 | 0.5 | 9:1 | 89.0 |
| 5 | 73 | 127 | 0.5 | 9:1 | 58.9 |
| 6 | 86 | 127 | 0.6 | 100% | 82.5 |
| 7 | 84 | 127 | 0.5 | 100% | 99.6 |
| 8 | 84 | 127 | 0.5 | 100% | 92.2 |
| 9 | 87 | 127 | 0.5 | 100% | 79.2 |
| 10 | 85 | 127 | 0.5 | 100% | 83.1 |
| 11 | 85 | 127 | 0.5 | 100% | 83.4 |
| 12 | 85 | 127 | 0.5 | 100% | 83.0 |
| 13 | 85 | 127 | 0.5 | 100% | 89.7 |
| 14 | 85 | 129 | 0.5 | 100% | 99.8 |
| 15 | 85 | 131 | 0.5 | 100% | 85.4 |
| 16 | 85 | 135 | 0.5 | 100% | 88.5 |
| 17 | 85 | 138 | 0.5 | 100% | 91.8 |
| 18 | 85 | 144 | 0.5 | 100% | 97.2 |
| 19 | 85 | 145 | 0.5 | 100% | 95.7 |
| 20 | 86 | 152 | 0.5 | 100% | 83.5 |
| 21 | 88 | 162 | 0.5 | 100% | 67.5 |
| 22 | 91 | 182 | 0.5 | 100% | 46.5 |
| 23 | 102 | 205 | 0.5 | 100% | 22.7 |
| 24 | 110 | 210 | 0.5 | 100% | 20.3 |
| 25 | 125 | 220 | 0.6 | 100% | 21.4 |
| 26 | 132 | 240 | 0.7 | 100% | 7.5 |

Fractions 7-20 of the foregoing distillation fractions are bulked and the bulking has an interesting peppery, guiacwood, vetiver aroma with sauge sclaree topnotes and musky undertones.

FIG. 39A is the GLC profile of the reaction product prior to distillation (2 hour sample).

FIG. 39B is the GLC profile of bulked fractions 7-20 evaluated according to the above organoleptic evaluation.

EXAMPLE VII

PREPARATION OF SUBSTITUTED METHYL ISOPROPYL CYCLOHEXENONE DERIVATIVE MIXTURE

Reaction

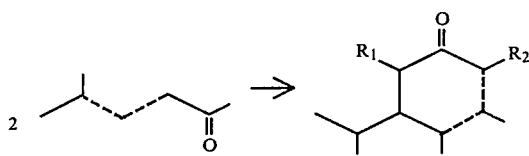

Into a 12 liter reaction flask equipped with thermometer, stirrer, addition funnel, reflux condenser and heating mantle is charged 250 grams of sodium hydroxide and 2000 ml anhydrous methanol. The resulting mixture is heated and maintained at 30° C. at which time 3 kg of 5-methyl-hexene-2-one prepared according to Example A is added to the reaction mass over a period of 1 hour. The reaction mass is then stirred at 30° C. until the reaction is complete as indicated by GLC. The reaction mass is then poured into 2000 ml water. The organic phase is separated from the aqueous phase and the organic phase is washed with water to a pH of 6-7. The resulting material is then distilled on a 4" Splash column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 27/110 | 112/126 | 3.0/2.5 | 71.9 |
| 2 | 122 | 134 | 2.5 | 84.5 |
| 3 | 125 | 137 | 2.5 | 90.8 |
| 4 | 127 | 140 | 2.5 | 87.2 |
| 5 | 128 | 142 | 2.5 | 86.7 |
| 6 | 129 | 143 | 2.5 | 90.7 |
| 7 | 133 | 144 | 2.5 | 92.6 |
| 8 | 133 | 144 | 2.5 | 93.1 |
| 9 | 133 | 145 | 2.5 | 95.1 |
| 10 | 133 | 145 | 2.5 | 93.6 |
| 11 | 134 | 146 | 2.5 | 90.9 |
| 12 | 134 | 147 | 2.5 | 92.4 |
| 13 | 134 | 147 | 2.5 | 94.7 |
| 14 | 134 | 148 | 2.5 | 92.5 |
| 15 | 134 | 148 | 2.5 | 114.1 |
| 16 | 134 | 148 | 2.5 | 93.5 |
| 17 | 134 | 152 | 2.5 | 91.6 |
| 18 | 135 | 154 | 2.5 | 93.1 |
| 19 | 136 | 158 | 2.4 | 93.0 |
| 20 | 137 | 164 | 2.4 | 90.6 |
| 21 | 140 | 170 | 2.4 | 93.7 |
| 22 | 150 | 178 | 2.5 | 91.7 |
| 23 | 154 | 190 | 2.5 | 21.4 |

The resulting distillation fractions 6-16 are then bulked and evaluated from an organoleptic standpoint. These fractions are evaluated as having a peppery, guiacwood, vetiver, sandalwood aroma with sauge sclaree topnotes and musky undertones.

FIG. 40A is the GLC profile of the reaction product prior to distillation.

FIG. 40B is the GLC profile of bulked fractions 6-16 of the foregoing distillation.

EXAMPLE VIII

PERFUME FORMULATION

The following sandal cologne perfume formulation is prepared:

| Ingredients | Parts by Weight |
|---|---|
| Bergamot oil | 200 |
| Orange oil | 150 |
| Lemon oil | 100 |
| Mandarin oil | 50 |
| Eugenol | 10 |
| 4-(4-methyl-4-hydroxy amyl) delta$^3$-cyclohexene carboxaldehyde | 30 |
| 3-methyl-4(2,6,6-trimethyl-2-cyclohexene-1-yl)-3-buten-2-one | 5 |
| methyl-N—3,7-dimethyl-7-hydroxy-octylidene anthranilate | 5 |
| 6,7-dihydro-1,1,2,3,3-pentamethyl-4-(5H)—indanone having the structure: prepared according to Prep. A of Swiss Patent 523,962 | 5 |
| 2-methyl-5(2-exo-methyl-3-methylene-bicyclo-[2.2.1]-hept-2-yl)3-penten-2-ol (prepared according to U.S. Pat. No. 4,000,050) | 100 |
| Mixture of substituted methyl isopropyl cyclohexenones prepared according to Example I, bulked fractions 7-22 | 40 |

The mixture of substituted methyl isopropyl cyclohexenones prepared according to Example I imparts to this sandal cologne formulation a warm, intense, peppery, guiacwood-like, vetiver, sandal odor with sauge sclaree topnotes and musky undertones.

EXAMPLE IX

LILAC PERFUME

The following mixture is prepared:

| Ingredients | Parts by Weight |
|---|---|
| Terpineol | 448 |
| Hydroxy citronellal | 113 |
| Heliotropin | 160 |
| Phenylethyl alcohol | 50 |
| Benzyl acetate | 82 |
| Anisaldehyde | 95 |
| Oil of cananga | 6 |
| Coumarin | 3 |
| Alpha ionone | 6 |
| Methyl jasmonate | 8 |
| 2,3-dimethyl-hydroquinone | 6 |
| p-methoxy acetophenone | 3 |

-continued

| Ingredients | Parts by Weight |
|---|---|
| Mixture of substituted isopropyl methyl cyclohexenones prepared according to Example III, bulked fractions 4-18 | 35 |

The addition of the substituted methyl isopropyl cyclohexenones produced according to Example III to this lilac formulation impart to it compatible fresh, floral, citrusy, and spicy aroma nuances which render it more aesthetically pleasing than the ordinary lilac formula and render it more "natural-like".

EXAMPLE X

PREPARATION OF A COSMETIC POWDER COMPOSITION

A cosmetic powder is prepared by mixing in a ball mill 100 grams of talcum powder with 0.25 grams of the perfume substance set forth in Table II below. The resulting substance has an excellent aroma as set forth in Table II below:

TABLE II

| Substance | Aroma |
|---|---|
| Mixture of substituted methyl isopropyl cyclohexenones prepared according to Example I, bulked fractions 7-22 | A peppery, guiacwood, vetiver, sandalwood, fruity, aroma with sauge sclaree topnotes and musky undertones |
| Product prepared according to Example II, bulked fractions 2-6 | A peppery, guiacwood, vetiver aroma with sauge sclaree topnotes |
| Product prepared according to Example III, bulked fractions 4-18 | A fresh, floral, citrusy, spicy aroma |
| Perfume composition of Example VIII | A sandalwood aroma with peppery, guiacwood, vetiver, musky and sauge sclaree nuances |
| Perfume composition of Example IX | A lilac aroma with fresh, floral, citrusy and spicy nuances |

EXAMPLE XI

PERFUMED LIQUID DETERGENT

Concentrated liquid detergents (lysine salt of n-dodecylbenzene sulfonic acid as more specifically described in U.S. Pat. No. 3,948,818 issued on Apr. 6, 1976, the specification for which is incorporated by reference herein) with aroma nuances as set forth in Table II of Example X supra are prepared containing 0.10%, 0.15% and 0.20% of the perfume substances as set forth in Table II of Example X. They are prepared by adding and homogeneously admixing the appropriate quantity of fragrance formulation as set forth in Table II of Example X in the liquid detergents. The detergents all possess excellent aromas as set forth in Table II of Example X, the intensities increasing with greater concentrations of perfume substance of Table II of Example X.

EXAMPLE XII

PREPARATION OF COLOGNES AND HANDKERCHIEF PERFUMES

Perfumery substances as set forth in Table II of Example X are incorporated into colognes in concentrations of 2.0%, 2.5%, 3.0%, 3.5%, 4.0%, 4.5% and 5.0% in 75%, 80%, 85%, 90%, and 95% aqueous food grade ethanol; and into handkerchief perfumes at concentrations of 15%, 20%, 25% and 30% (in 80%, 85% and 95% aqueous food grade ethanol). Distinctive and definitive aromas as set forth in Table II of Example X are imparted to the cologne and to the handkerchief perfume at all the levels indicated above.

EXAMPLE XIII

PREPARATION OF SOAP COMPOSITIONS 100 grams of soap chips (IVORY ® produced by the Procter & Gamble Company, Cincinnati, Ohio) are mixed with one gram of each of the substances as set forth in Table II of Example X supra, until homogeneous compositions are obtained. In each of the cases, the homogeneous compositions are heated under 8 atmospheres pressure at 180° C. for a period of 8 hours. The resulting liquids are placed into soap molds. The resulting soap cakes, on cooling, manifest aromas as set forth in Table II of Example X.

EXAMPLE XIV

PREPARATION OF SOLID DETERGENT COMPOSITIONS

Detergents are prepared from the following ingredients according to Example I of Canadian Patent No. 1,007,948, the specification for which is incorporated by reference herein:

| Ingredients | Parts by Weight |
|---|---|
| Neodol ® 45-11 (a $C_{14-15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent per sample is admixed with 0.15 grams of each of the perfume substances of Table II of Example X. Each of the detergent samples has excellent aromas as set forth in Table II of Example X.

EXAMPLE XV

Utilizing the procedure of Example I at column 15 of U.S. Pat. No. 3,632,396 (the specification for which is incorporated by reference herein), a non-woven cloth substrate useful as a drier-added fabric softening article of manufacture is prepared wherein the substrate, the substrate coating and the outer coating and the perfuming material are as follows:
1. a water dissolvable paper as the substrate ("Dissolvo Paper")
2. Adogen 448 (melting point 140° F.) as the substrate coating and
3. an outer coating having the following formulation (melting point about 150° F.):
   57% $C_{20-22}$ HAPS
   22% isopropyl alcohol
   20% antistatic agent
   1% of one of the per fumery substances as set forth in Table II of Example X A fabric softening composition prepared as set forth above having aroma characteristics as set forth in Table II of Example X consists of a substrate having a weight of about 3 grams per 100 square inches, a substrate coating weighing about 1.85 grams per 100 square inches of substrate and an outer coating weighing about 1.4 grams per 100 square inches of substrate is created, thereby providing a total aromatized substrate and outer coating weight ratio of about 1:1 by weight of the substrate. The aromas as set forth in Table II of Example X is imparted in pleasant manners to head spaces in the driers on operation thereof using the drier-added fabric softening non-woven fabric articles.

EXAMPLE XVI

A tobacco blend is made up by mixing the following materials:

| Ingredients | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes:

| Ingredients | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the substituted methyl isopropyl cyclohexenone mixture produced according to Example I, bulked fractions 11–19 at 400 ppm per cigarette. Another one-third of these model cigarettes are treated in the filter with bulked fractions 11–19 of the methyl isopropyl cyclohexenone mixtures produced according to Example I at the rate of $2 \times 10^{-4}$ grams. When evaluated by paired comparison, the cigarettes treated both in the tobacco and in the filter with the substituted methyl isopropyl cyclohexenone derivatives prepared according to Example I are found, in smoke flavor, to be more tobacco-like with enhanced sweet, citrusy characteristics.

Prior to smoking, the tobacco composition has a woody, peppery, citrusy aroma profile. The sweet, citrusy character in the smoke flavor is imparted both in the main stream and in the side stream on smoking.

What is claimed is:

1. A process for augmenting or enhancing the aroma or taste of a consumable material selected from the group consisting of smoking tobacco compositions and smoking tobacco article components comprising the step of adding to consumable material an aroma or taste augmenting or enhancing quantity of at least one compound defined according to the structure:

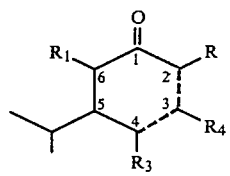

wherein one of the dashed lines represents a carbon-carbon double bond and the other of the dashed lines represents a carbon-carbon single bond; wherein $R_4$ represents methyl or ethyl; wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:

(i) when the dashed line at the 3-4 position is a double bond, then $R_3$ is hydrogen or 2-methyl-1-propenyl;

(ii) when the dashed line at the 2-3 position is a double bond, then $R_2$ is hydrogen or 2-methyl-1-propenyl;

(iii) when $R_4$ is ethyl, then $R_2$ is methyl and the double bond is at the 2-3 position; and (iv) when $R_4$ is methyl, then $R_2$ is hydrogen; 2-methyl-1-propenyl or 2-methyl-1-propylidenyl;

with the members of said genus being novel compounds when $R_4$ is ethyl or when $R_4$ is methyl and the double bond is at the 3-4 position or when $R_4$ is methyl and the double bond is at the 2-3 position with $R_3$ being hydrogen.

2. The process of claim 1 wherein the consumable material is a smoking tobacco composition.

3. The process of claim 1 wherein the consumable material is a component of a smoking tobacco article.

* * * * *